US008696595B2

(12) United States Patent
Sangha

(10) Patent No.: US 8,696,595 B2
(45) Date of Patent: Apr. 15, 2014

(54) UNITIZED SYSTEM FOR COLLECTION, DRYING TRANSPORT AND ANALYSIS

(75) Inventor: Jangbir Sangha, Overland Park, KS (US)

(73) Assignee: The Bode Technology Group, Inc., Lorton, VA (US)

( * ) Notice: Subject to any disclaimer, the term of this patent is extended or adjusted under 35 U.S.C. 154(b) by 503 days.

(21) Appl. No.: 12/714,477

(22) Filed: Feb. 27, 2010

(65) Prior Publication Data
US 2011/0004122 A1    Jan. 6, 2011

Related U.S. Application Data

(60) Provisional application No. 61/305,497, filed on Feb. 17, 2010, provisional application No. 61/172,771, filed on Apr. 26, 2009.

(51) Int. Cl.
*A61B 10/00* (2006.01)
*A61M 35/00* (2006.01)

(52) U.S. Cl.
USPC ............... 600/572; 600/562; 600/569; 604/1

(58) Field of Classification Search
USPC .................................. 600/562–572
See application file for complete search history.

(56) References Cited

U.S. PATENT DOCUMENTS

| | | |
|---|---|---|
| 4,014,748 A | 3/1977 | Spinner |
| 4,175,008 A | 11/1979 | White |
| 4,211,323 A | 7/1980 | Olsen |
| 4,223,093 A | 9/1980 | Newman |
| 4,813,432 A | 3/1989 | Saint-Amand |
| 4,873,193 A | 10/1989 | Jensen |
| 4,917,867 A | 4/1990 | Jensen |
| 5,856,172 A | 1/1999 | Greenwood |
| 6,187,269 B1 | 2/2001 | Lancesseur |
| 2002/0057991 A1 | 5/2002 | Kelly |
| 2004/0082878 A1 | 4/2004 | Baldwin |
| 2005/0009200 A1 | 1/2005 | Guo |
| 2007/0255175 A1 | 11/2007 | Sangha |
| 2007/0299364 A1 | 12/2007 | Sangha |
| 2008/0206740 A1 | 8/2008 | Skiffington |
| 2008/0254550 A1 | 10/2008 | Nathaniel |
| 2009/0043226 A1 | 2/2009 | Elwell |
| 2009/0215159 A1 | 8/2009 | Kirby |

*Primary Examiner* — Max Hindenburg
*Assistant Examiner* — Adam Eiseman
(74) *Attorney, Agent, or Firm* — Richard Stitt; Poisinelli PC

(57) ABSTRACT

A unitized apparatus for collection and/or drying and/or transport and/or analysis of a specimen is provided having a desiccant chamber that permits variable quantities of desiccant to be loaded into the device and to allow the desiccant to be recharged within the device without contacting or causing damages to the specimen collected thereon.

19 Claims, 19 Drawing Sheets

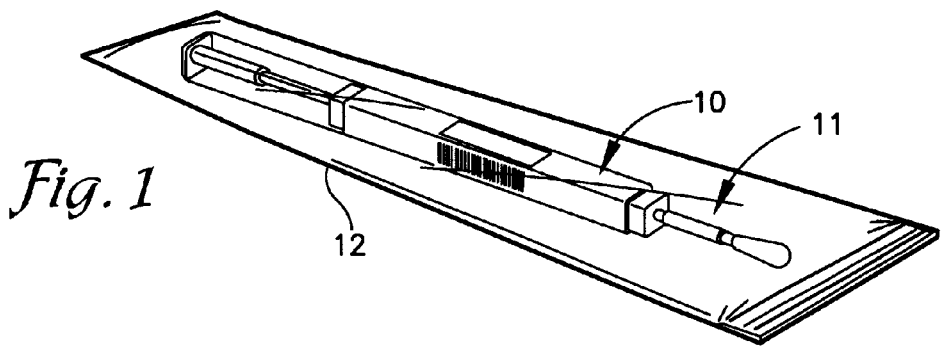
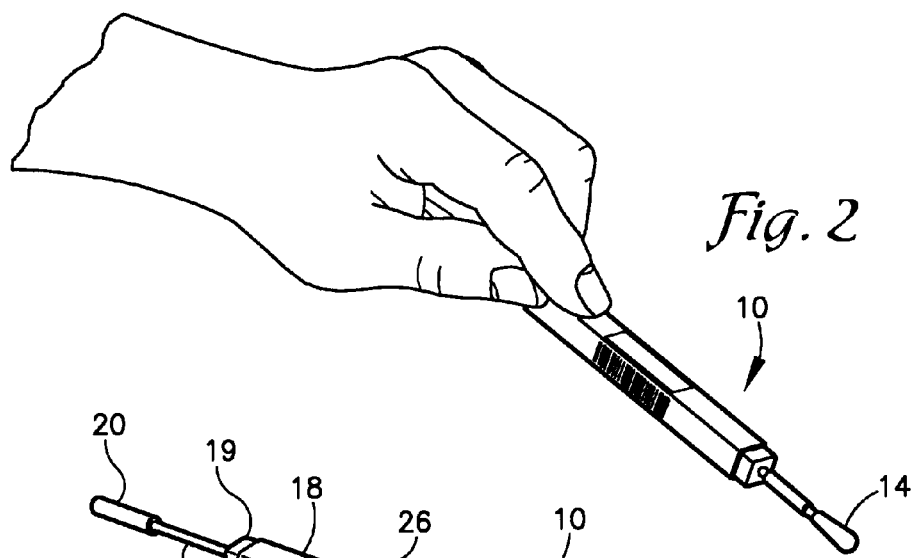
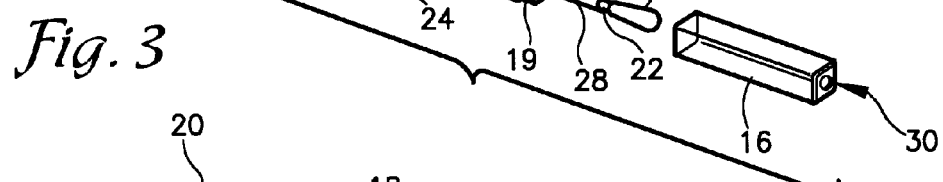
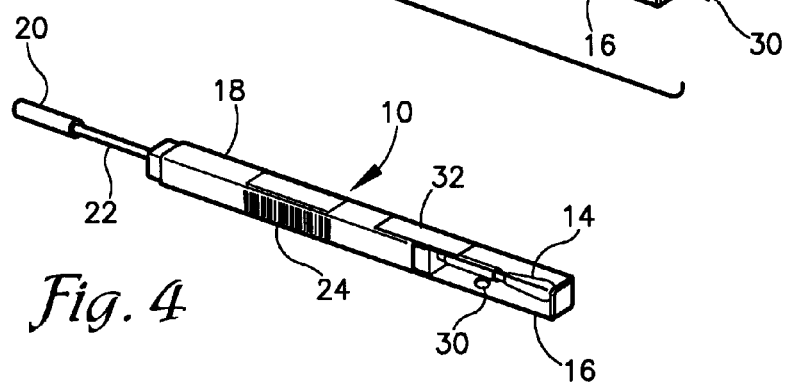

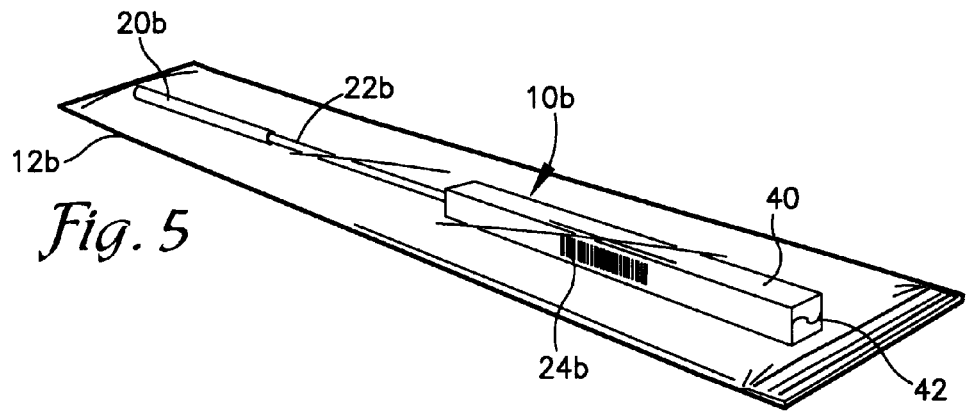
Fig. 5
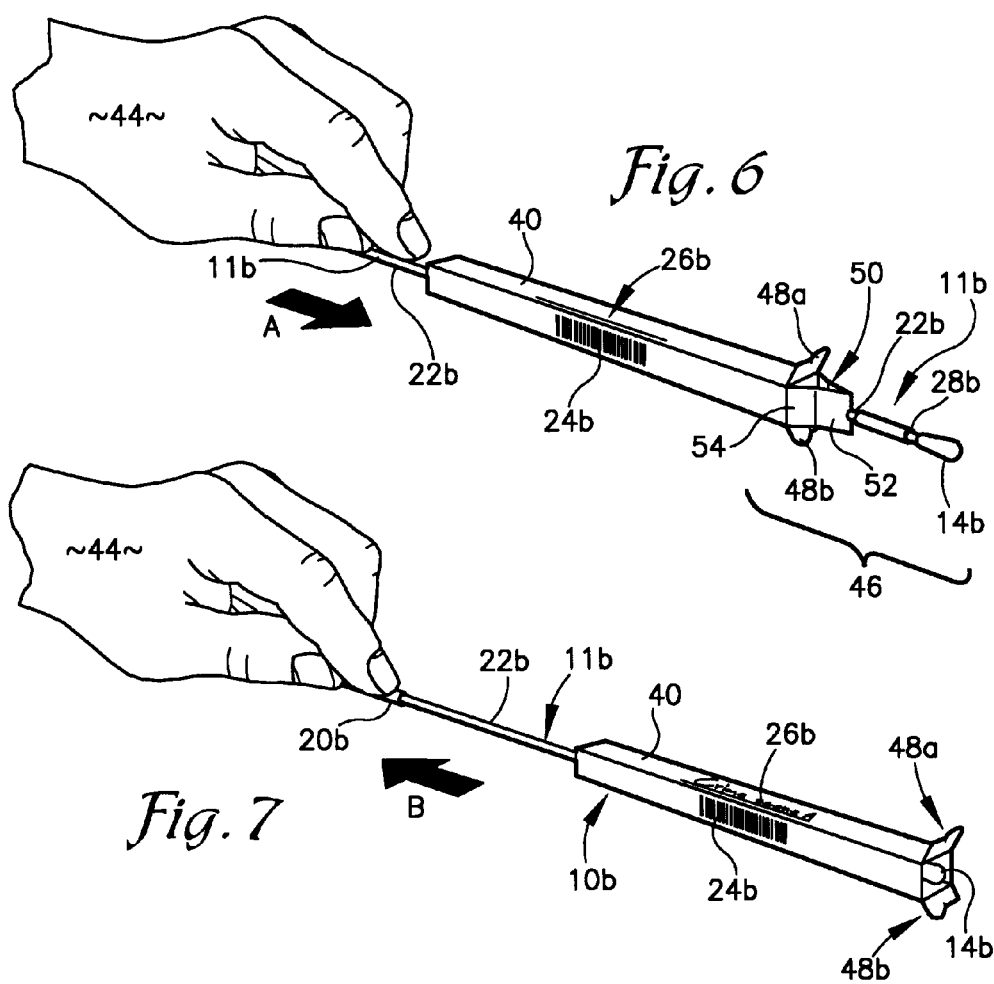
Fig. 6
Fig. 7

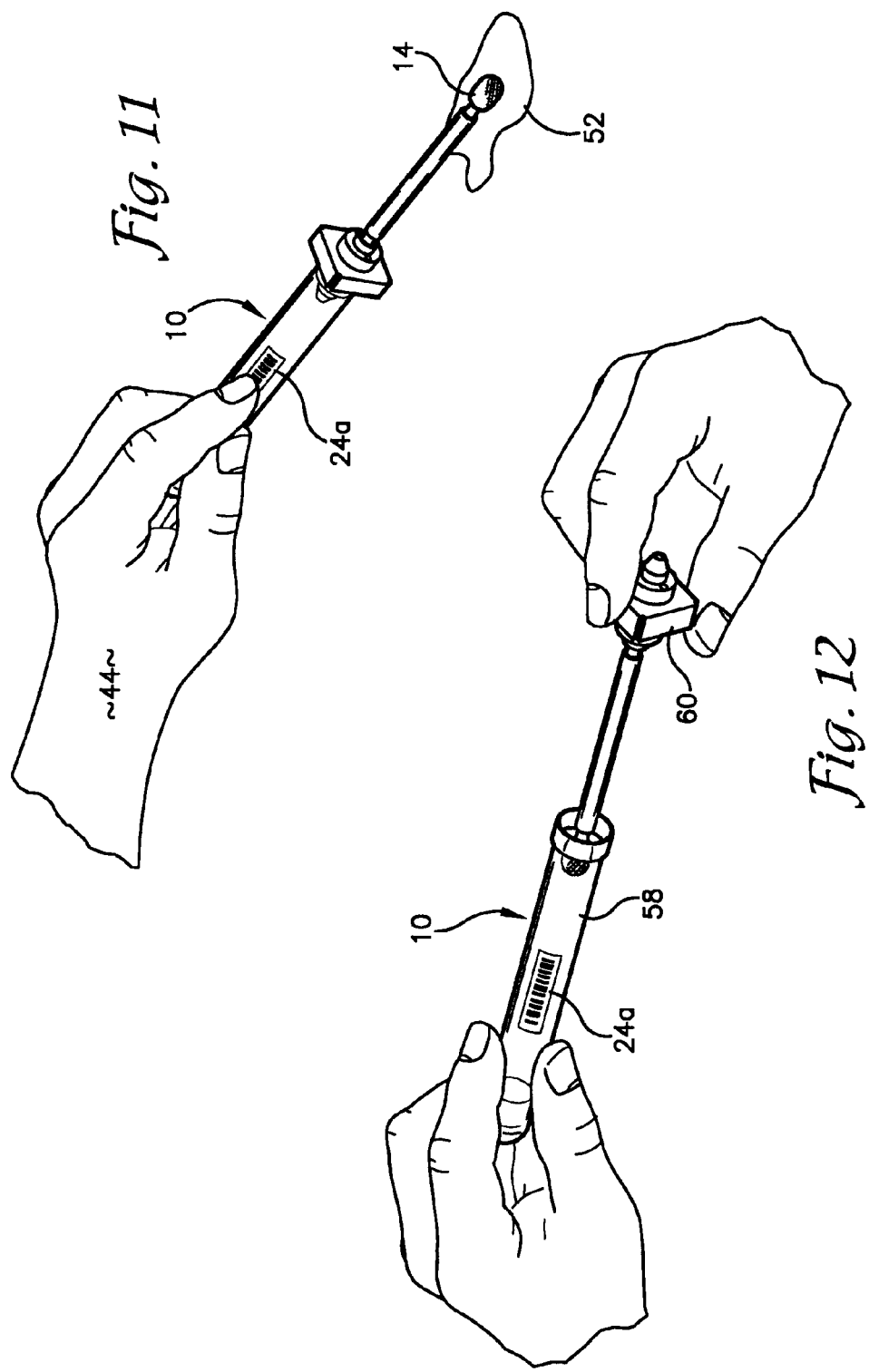

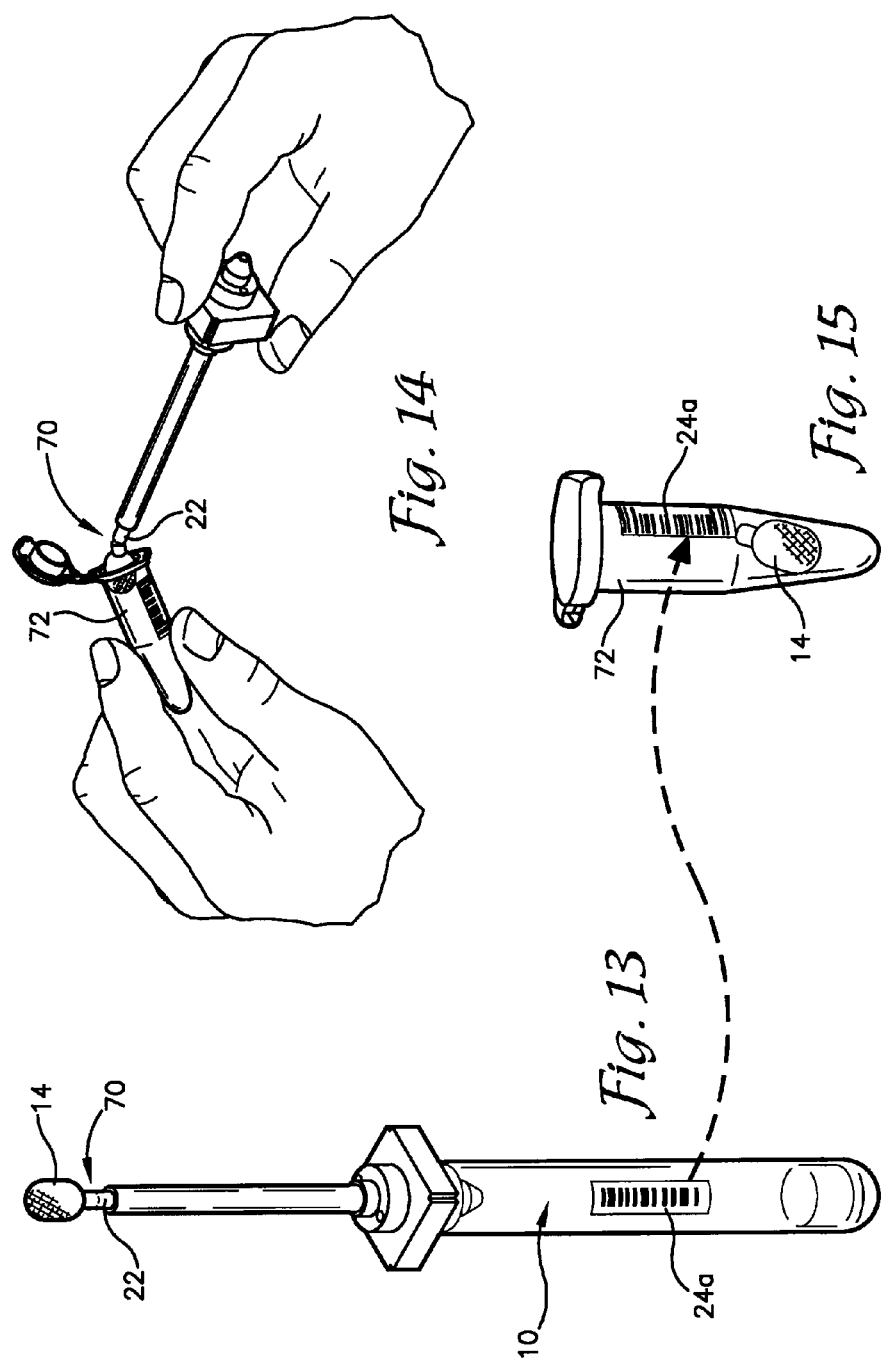

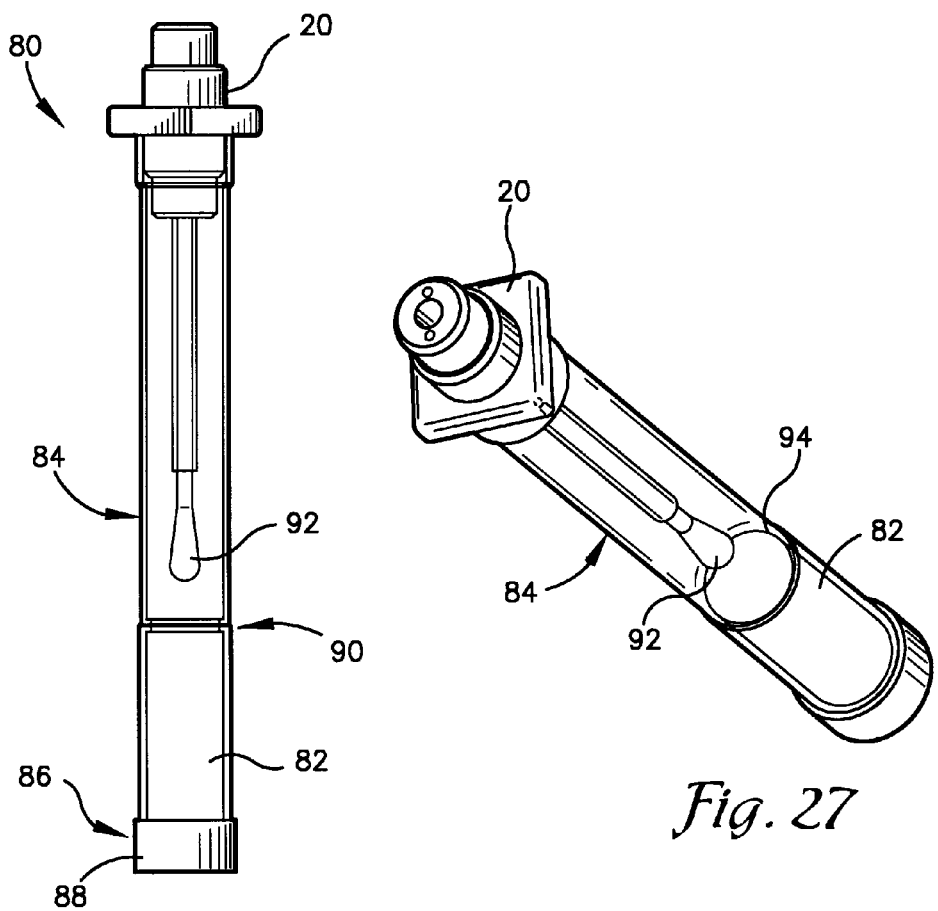
Fig. 26
Fig. 27
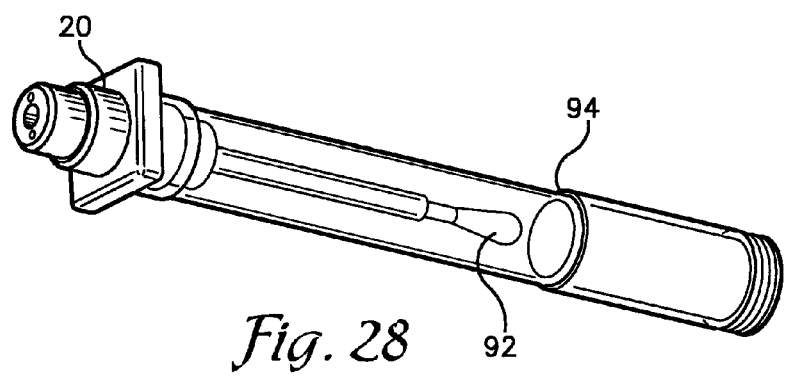
Fig. 28

UNITIZED SYSTEM FOR COLLECTION, DRYING TRANSPORT AND ANALYSIS

CROSS REFERENCE TO RELATED APPLICATION

This application claims priority under 35 U.S.C. 119(e) and 37 C.F.R. 1.78(a)(4) based upon U.S. Provisional Application Ser. No. 61/305,497 filed Feb. 17, 2010, U.S. Provisional Application Ser. No. 61/172,771 filed Apr. 25, 2009, based upon copending U.S. patent application Ser. No. 11/699,807 filed Jan. 30, 2007 based upon U.S. Provisional Application Ser. No. 60/815,801 filed Jun. 22, 2006 and U.S. patent application Ser. No. 11/653,116 filed Jan. 12, 2007 based upon U.S. Provisional Application Ser. No. 60/758,855 filed Jan. 13, 2006 and U.S. patent application Ser. No. 11/787,313 filed Apr. 16, 2007 based upon U.S. Provisional Application Ser. No. 60/792,057 filed Apr. 14, 2006 all of which are incorporated herein by reference.

FIELD OF THE INVENTION

The field of the invention is directed to apparatus and methods for collection and transport and analysis of evidence samples and the method of preparing such evidence or samples for forensic analysis. In particular embodiments of devices for collection of evidence are provided and methods of extracting such evidence from the collection device prior to laboratory analysis.

BACKGROUND OF THE INVENTION

The present embodiment provides a specimen collection and drying and transport and storage device that can be used for laboratory and forensic purposes to gather samples and specimens and to then dry the sample and/or specimen during transport and/or storage prior to testing of the sample or specimen.

The present embodiments relates to the collection of material samples, as for forensic, scientific, or diagnostic purposes, and more particularly, to containerized, low pressure sample collection apparatus for collecting such samples and preserving them from contamination prior to laboratory analysis, that is, such apparatus in which the sample carrying member is enclosed after collection of the sample to protect the sample from contamination.

Crime scene evidence is collected to establish facts related to a crime or a suspected crime and for identification and/or elimination of suspects and may be presented at a trial for the determination of guilt or innocence of accused individuals. Often, the evidence includes objects, documents, fingerprints, photographs of the scene, and the like. Additionally, the evidence may include unknown substances or substances with a suspected identity, where the identity needs to be determined or confirmed. Such substances may be very small in quantity, may be dispersed over a comparatively large area, and may include materials such as: body fluids, hairs, flakes of skin, fibers, drugs, various chemicals, gunpowder residue, flammable materials, tobacco ashes, cosmetics, and the like. Such materials may be collected at a scene and subjected to chemical and/or DNA analysis for identification or for association with a particular individual.

For collecting substance samples, investigators typically use fibrous swabs, such as swabs made of fibers of cotton, cellulose, rayon, polyester, and other types of fibers. Such swabs not only absorb liquids and solids entrained in liquids but also trap dry substances such as particulate materials. The swabs are kept in closed bags or containers prior to use to maintain sterility and are replaced in such containers after use to avoid contamination of the sample gathered. After replacement of a swab in a container, the container is usually marked with a time and date and identity of the investigator and other information to establish a chain of custody of the sample.

Conventional swabs are formed of a "stick" such as a shaft of wood, tubular plastic, or tubular or rolled paper with a pad of cotton or other fiber, sponge material, or other absorbent material attached to the end of the shaft, either mechanically or by an inert adhesive. A problem with conventional swabs is that there is a danger of contamination of the sample if it is necessary to put the swab down, for example, to open a bag or container in which the swab will be placed. Also, if it is necessary to set the swab down to dry, in a propped up condition or extending over the edge of a table, there is a risk of contamination of the sample.

The present embodiments relates to the collection of material samples, as for forensic, scientific, or diagnostic purposes, and more particularly, to devices for collecting such samples and preserving them from contamination prior to laboratory analysis.

Crime scene evidence is collected to establish facts related to a crime or a suspected crime and for identification and/or elimination of suspects and may be presented at a trial for the determination of guilt or innocence of accused individuals. Often, the evidence includes objects, documents, fingerprints, photographs of the scene, and the like. Additionally, the evidence may include unknown substances or substances with a suspected identity, where the identity needs to be determined or confirmed. Such substances may be very small in quantity, may be dispersed over a comparatively large area, and may include materials such as: body fluids, hairs, flakes of skin, fibers, drugs, various chemicals, gunpowder residue, flammable materials, tobacco ashes, cosmetics, and the like. Such materials may be collected at a scene and subjected to chemical and/or DNA analysis for identification or for association with a particular individual.

For collecting substance samples, investigators typically use fibrous swabs, such as swabs made of fibers of cotton, cellulose, rayon, polyester, and other types of fibers. Such swabs not only absorb liquids and solids entrained in liquids but also trap dry substances such as particulate materials. The swabs are kept in closed bags or containers prior to use to maintain sterility and are replaced in such containers after use to avoid contamination of the sample gathered. After replacement of a swab in a container, the container is usually marked with a time and date and identity of the investigator and other information to establish a chain of custody of the sample.

Conventional swabs are formed of a "stick" such as a shaft of wood, tubular plastic, or tubular or rolled paper with a pad of cotton or other fiber, sponge material, or other absorbent material attached to the end of the shaft, either mechanically or by an inert adhesive. A problem with conventional swabs is that there is a danger of contamination of the sample if it is necessary to put the swab down, for example, to open a bag or container in which the swab will be placed. Also, if it is necessary to set the swab down to dry, in a propped up condition or extending over the edge of a table, there is a risk of contamination of the sample.

As set forth in the previously filed specifications to which the present application claims priority the present embodiment is a continuation-in-part of those applications the description of the subject matter of which is now contained in this provisional application both by reference and by the addition of that specification material directly into this provisional application filing.

The present embodiments relates to an apparatus and method for collecting what is known as "touch evidence" related to any type of situation in which evidence collection is required. Such evidence collection can be associated with crime scenes or can simply be the collection of a DNA sample from a human being in the course of a traffic stop or a paternity investigation. Touch evidence, in general, is that evidence which is located on a surface or on a human being and which can be physically contacted by an evidence collection device to thereby obtain a sample of the evidence. Examples of such touch evidence might be any type of biological fluid, either wet or dried, such as blood, urine or saliva, or any unknown substance which is visible or invisible and which can be located allowing for collection of a specimen of the evidence and capture of such a sample on a touch evidence collector of the type described hereinafter. As previously mentioned, it will be appreciated that such touch evidence collection devices are widely used in criminal investigations, but also are used increasingly in traffic stop situations or traffic arrest situations in which it is desirable to obtain a DNA sample from the suspect as part of a criminal records database requirement.

SUMMARY OF THE INVENTION

The present embodiments provides a greatly improved sample or specimen collection apparatus and a low pressure sample collection apparatus. Generally the sample collection apparatus includes an elongated tubular shaft having a swab member secured to a swab end thereof. In one embodiment air is drawn through the shaft from the swab end toward an opposite vacuum connection end of the shaft flows through the swab. A housing is positioned between the ends of the shaft and forms a handle to enable manipulation of the apparatus to collect a sample of a substance. Preferably, the apparatus includes a cap member which can be connected to the housing in covering relation to the swab member to protect it from contamination and which can be stored on an opposite end of the housing. The cap may have one or more holes or apertures formed in its side wall to admit air to dry the swab member when the cap covers the swab member. The cap may also have a desiccant positioned therein to facilitate drying the swab member or the desiccant may be positioned in the tube bottom (FIG. 10).

Some part of the sample collection apparatus is marked with unique identification indicia to distinguish one apparatus from another. Preferably, such identification indicia is applied to the housing. The indicia can be in the form of a barcode, a serial number, or the like. The housing may also have a writable surface, such as a paper tag adhered thereto so that an investigator or technician may write identifying notes on the apparatus, such as initials, a date, a time, a case number, or the like. The apparatus may have a push-off barrel telescoped on the tubular shaft between the housing and the swab member. The barrel is grasped and pushed against the swab member to separate the swab member from the shaft without touching, and possibly contaminating a sample on the swab member, for example for laboratory analysis. Alternatively, the shaft can be scored or be made of a breakable material to allow separation of the swab when the swab is pressed against a side wall of a tube.

The housing may have any cross-sectional shape. A non-round shape resists rolling if the apparatus is placed on a surface. The cross-sectional shape may be rectangular, square, circular, or any other suitable shape. Preferably, ends of the housing have reduced cross-sectional areas to form plugs to receive an open end of the cap member. The sample collection apparatus may be used to collect liquid or dry samples. A portable, low pressure vacuum unit may be connected to the vacuum connection end of the shaft to establish inward air flow through the swab member to facilitate collection of dry samples, such as particulate or flaked materials. Alternatively, the sample collection apparatus may be used without such a vacuum unit.

A modified slide-out embodiment of the sample collection apparatus provides a swab assembly which can be retracted into a housing to protect a swab member from contamination. The apparatus includes an elongated tubular shaft having a swab member secured to a swab end and has an opposite vacuum connection end. The shaft is slidably mounted through a tubular housing member by means of a centering structure which maintains the swab member out of contact with walls of the housing when retracted therein. The housing has flap members at a swab end thereof which can be closed to protect the swab member from contamination. The shaft, swab member, and centering structure form a swab assembly which is slidable through the housing. The swab assembly is advanced to an extended position to extend the swab member out of the housing to collect a sample. The swab assembly is retracted to retract the swab member within the housing, after which the flaps may be closed to protect a sample collected on the swab member from contamination. The shaft may include a push-off barrel positioned between the centering structure and the swab member. The barrel can be used to separate the swab member from the shaft without touching the swab member. The housing is preferably provided with unique identification indicia, such as a barcode, serial number, or the like. Additionally, the housing may be provided with a writable surface to receive notes from an investigator or technician.

Also taught is a method of forensic specimen collection which provides for a specimen collector having a unique barcode thereon within a clear plastic wrapper; the wrapper having multiple copies of the identical unique barcode which is on the collector. The clear packaging permits the crime scene investigator to photograph the unopened collector next to the specimen to be collected, thus recording the series of barcodes adjacent the specimen prior to collection. The additional barcodes allow the investigator to use the additional barcodes to cross-reference the specimen with notes in a notebook and to cross-reference a tamper-proof seal applied to the specimen container after specimen collection thereon, and to cross-reference any transportation packaging used to ship the collector having the specimen thereon to a laboratory for analysis.

Objects and advantages will become apparent from the following description taken in conjunction with the accompanying drawings wherein are set forth, by way of illustration and example, certain embodiments of this invention.

The device provides an improved low pressure sample collection apparatus for collecting samples of substances and protecting such samples from contamination prior to laboratory analysis. Generally, the sample collection apparatus includes a swab assembly including an elongated shaft, a swab member secured to an end of the shaft, and a cap member connected to an end of the shaft opposite the swab member. The cap member has plug members on opposite sides of a central portion thereof to enable the cap member to be plugged into a container member either with the swab member exposed or with the swab member positioned within and protected from contamination within the container member. The cap member may be provided with one or more bores to allow the influx of drying air into the container with the swab member therein to promote drying of a sample on the swab member. Preferably, the shaft is tubular and the cap member has a nipple on a side opposite from the shaft for connection of a low pressure vacuum source to establish an inflow of air through the swab member to thereby facilitate collection of samples onto and within the swab member.

The shaft may include a push-off barrel positioned between the cap member and the swab member for gripping to push the swab member off the shaft for analysis without contaminating any sample on the swab member. The shaft may further include a drying disk encircling the shaft to prop the swab member off a surface on which the sample collection apparatus is placed to allow the swab member to dry. Because the sample collection apparatus is intended for forensic evidence collection, it is necessary for a chain of custody to be established for any sample collected using the apparatus. For this purpose, the container member and the swab assembly are preferably marked with unique identifying indicia, such as matching barcodes, serial numbers, or the like. Such indicia may be provided by adhesively backed paper labels or by etching into the surfaces of the container member and components of the swab assembly. On the swab assembly, the indicia can be applied on the cap member, the shaft, or the push-off barrel if present.

The sample collection apparatus may include casings positioned on the shaft and including a portion which is positioned in surrounding relation to the swab member to control the flow of air about the swab member during sample collection. In general, the casings are slidably positioned on the shaft using a packing member to slide between a retracted position exposing the swab member, as for drying or removal, and an extended position to shroud the swab member. In one embodiment of a swab casing, the casing has a porous region, formed by fritted glass or the like, which allows some air to flow in toward the swab member from the sides, in addition to air which flows through the end of the casing. In another embodiment of a swab casing, the casing is cylindrically expanded at an outer end to a diameter which is somewhat larger than that of the swab member. Finally, a flared embodiment of a swab casing has a flared end, such as a conically flared end, in the region adjacent the swab member.

The present embodiment provides a sample collection and drying and transportation and storage device having a portion that operates as a handle during collection and which portion operates as a stand for keeping the specimen on the swab spaced from the surrounding surfaces and which is equipped with desiccant areas immediately adjacent the swab during storage to speed the drying of the swab and to permit insertion of different quantities or volumes of desiccant into the device to permit faster or slower drying of moisture on the swab as is selected by the user.

The flexible guard structures of the device further operate to keep the swab and the specimen thereon spaced from contact with the desiccant material inserted into the desiccant housing. The desiccant housing has separate accessibility via a desiccant chamber cap that permits the user to insert or change out or replace or increase or decrease the amount of desiccant used in the device as it may become advantageous during the sample processing.

Embodiments of the present invention also show a cap that provides the ability to use, with one hand, dual swabs which may be used to collect both a wet-swab specimen and a dry-swab specimen utilizing the same apparatus and without changing collection devices and while collecting the wet-swab specimen and the dry-swab specimen nearly simultaneously with one hand.

Yet another embodiment shows a cap that provide the ability to collect a single swab sample on one side of the cap and a dual or wet-swab specimen and a dry-swab specimen sample on the other side of the cap.

DESCRIPTION OF THE DRAWINGS

The drawings constitute a part of this specification and include exemplary embodiments of the present invention and illustrate various objects and features thereof.

FIG. 1 is a perspective view of a sample collection apparatus which is positioned in a sealable bag;

FIG. 2 is a perspective view of the sample collection apparatus removed from the bag of FIG. 1 for use in the field to collect a sample of a substance;

FIG. 3 is a perspective view of the sample collection apparatus with a cap removed to expose a vacuum connection, the cap being positioned to cover a swab member after a sample has been collected;

FIG. 4 is a perspective view of the sample collection apparatus with the cap in covering relation to the swab member and diagrammatically showing an aperture in the cap to facilitate drying of the swab member;

FIG. 5 is a perspective view of a slide-out embodiment of the sample collection apparatus shown positioned in a sealable bag;

FIG. 6 is a perspective view of the slide-out sample collection apparatus, shown with a swab member extended for use in the field to collect a sample of a substance;

FIG. 7 is a perspective view of the slide-out sample collection apparatus, shown with the swab member being retracted into an integral housing of the apparatus;

FIG. 11 shows a collector being applied to a crime scene specimen for collection of a specimen onto the absorbent of the collector;

FIG. 12 shows the absorbent collector having the specimen adhered to the absorbent being inserted into the container or housing used to protect the absorbent from cross-contamination after specimen collection;

FIG. 13 shows a specimen collector having a scored shaft line adjacent the collection absorbent;

FIG. 14 shows the collector absorbent of the collector of FIG. 13 being pressed against the sidewall of a microspecimen vial to separate the absorbent along the score line;

FIG. 15 shows the absorbent of FIGS. 13 and 14 now separated from the shaft of the collector of FIGS. 13 and 14 and with the absorbent residing within the microspecimen container for analysis of the specimen and with a line indicating transfer of the unique barcode from the container of FIG. 13 onto the micro-vial of FIG. 15 for maintenance of the chain of custody.

FIG. 26 is a side elevation view of a fifth modified embodiment of the sample collection apparatus having a secondary chamber included in the casing and extending from the portion of the casing containing the swab, the secondary chamber having an openable and closable first end having a cap thereon and the second end of the secondary chamber being in atmospheric communication with the portion of the casing containing the swab.

FIG. 27 is a top and side perspective view of the fifth modified embodiment of the sample collection apparatus of FIG. 26.

FIG. 28 is a top and side perspective view of the fifth modified embodiment of the sample collection apparatus of FIG. 26 showing the cap removed to permit independent access to the secondary chamber.

Drawings Descriptions of the Unitized Apparatus Embodiment

Figures 30, 31:
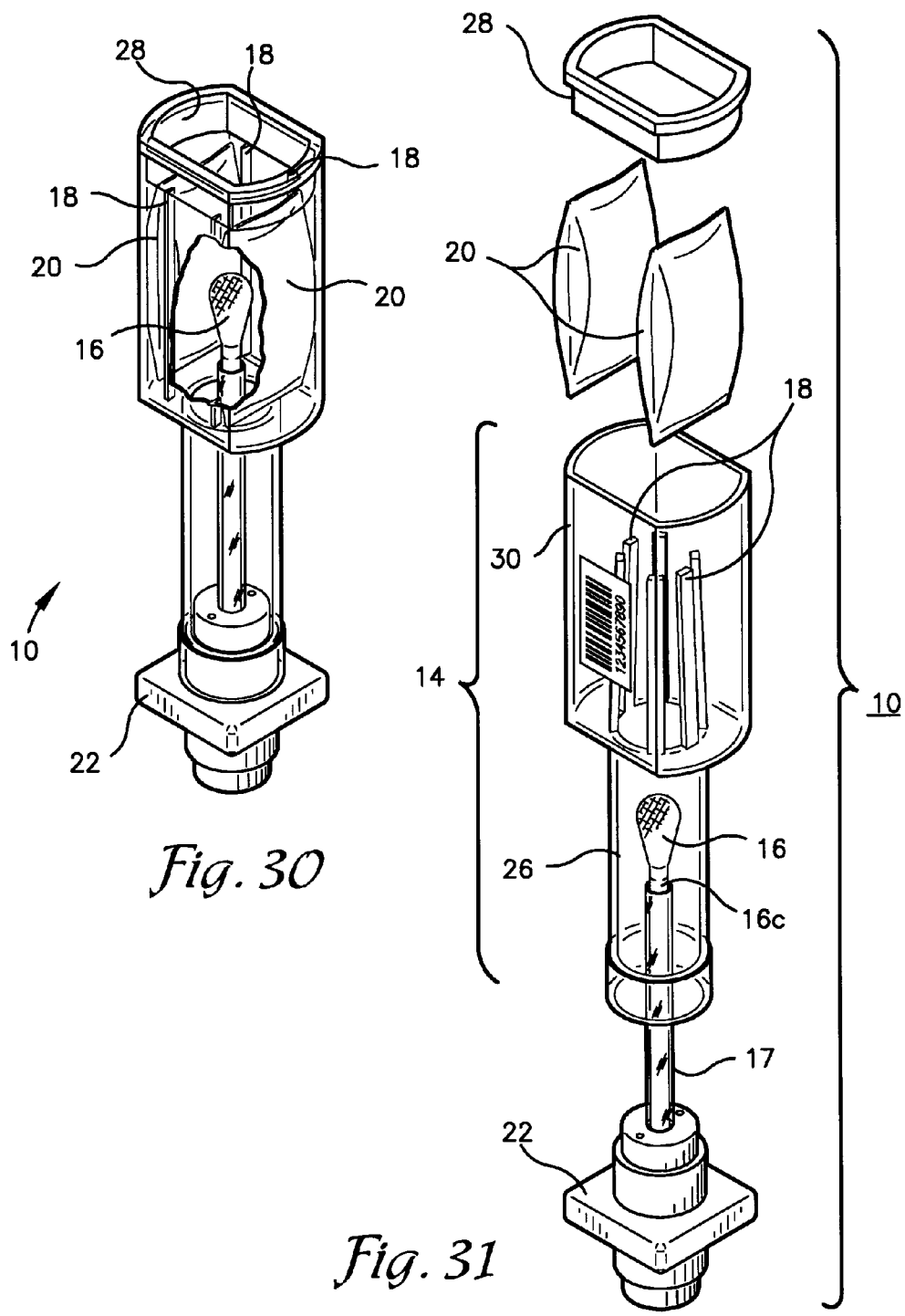
Figures 32, 33:
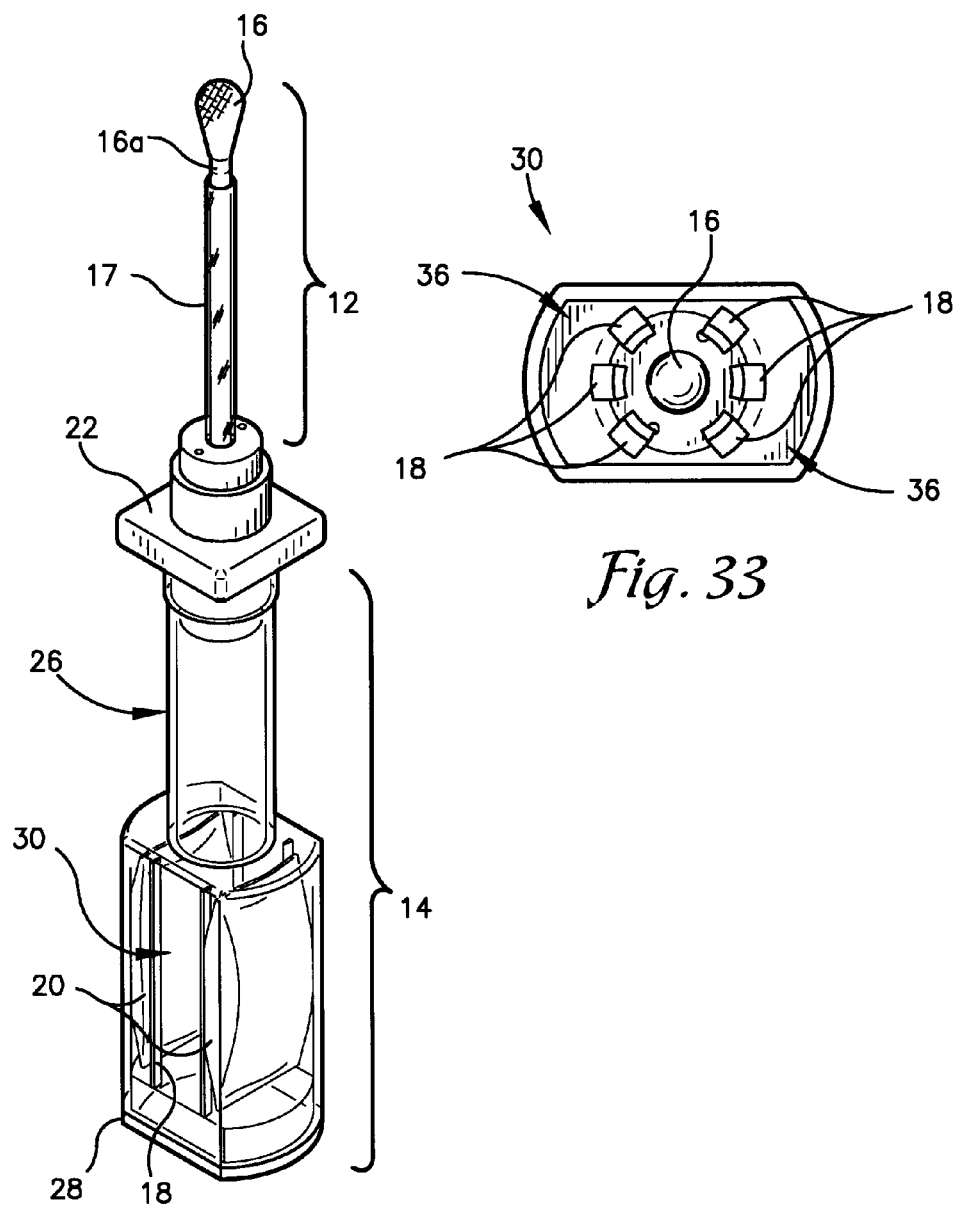

FIG. 30 is a bottom and left side perspective view of an embodiment 10 showing one example of the embodiment in its closed position with the specimen collector 12 within the housing 14 and the swab 16 situated within the flexible guards 18 and between two desiccant packets 20;

FIG. 31 shows an exploded view of the embodiment of FIG. 30;

FIG. 32 shows the embodiment of FIG. 30 with specimen collector 12 reversed and with the cap 22 inserted into opening 24 of the neck 26 of the housing 14 to allow the housing 14 to act as a handle for manipulating the swab 16 of the specimen collector portion 12;

FIG. 33 is a bottom end view into desiccant chamber 30 of the embodiment of FIG. 30 and showing the swab 16 within flexible guards 18 and spaced therefrom to hold swab 16 and any specimen thereon away from desiccant packets 20 during drying and/or transport and/or storage;

Drawing Descriptions Turbo Janus Gemini

Figures 34, 35:
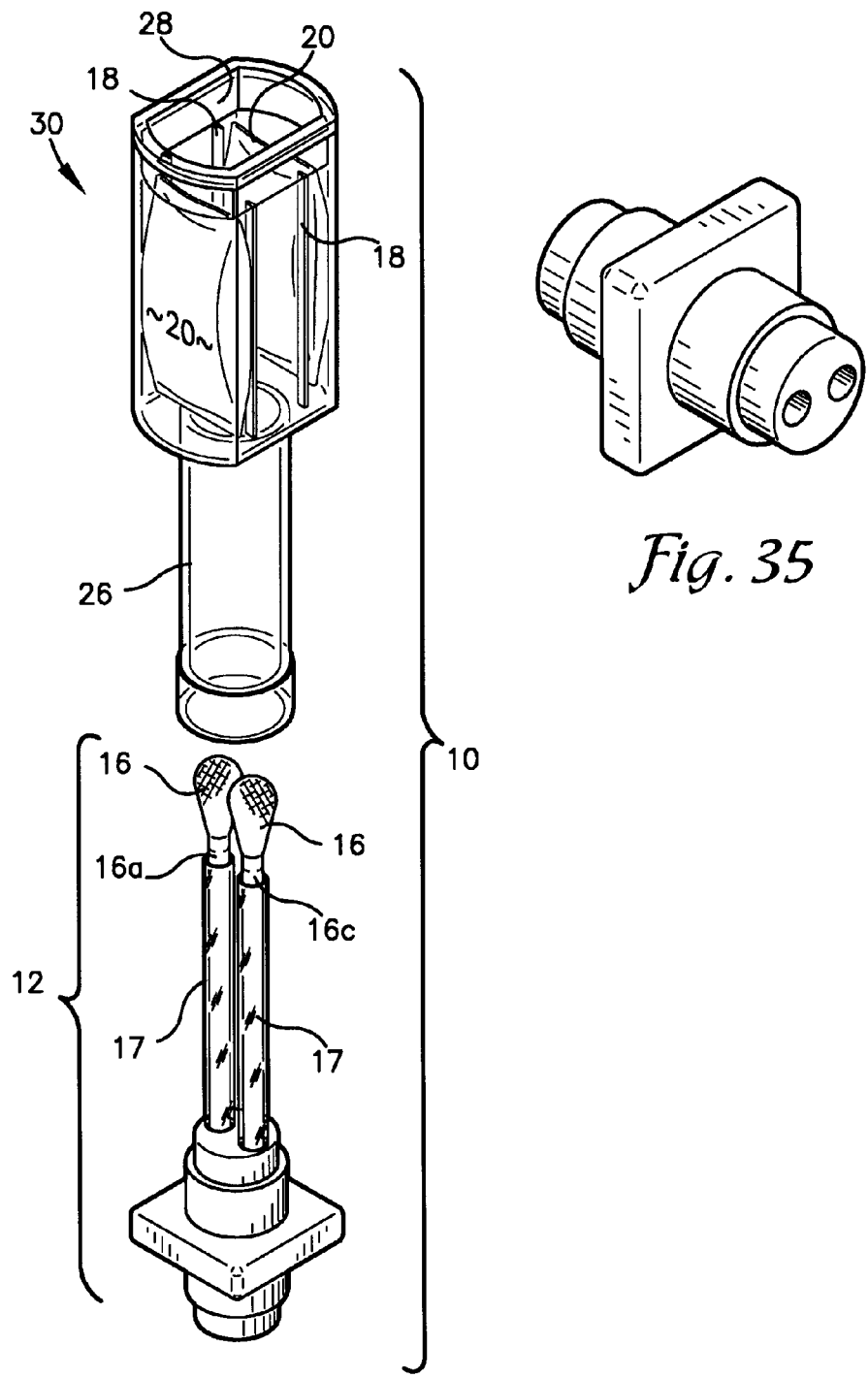
Figure 36:
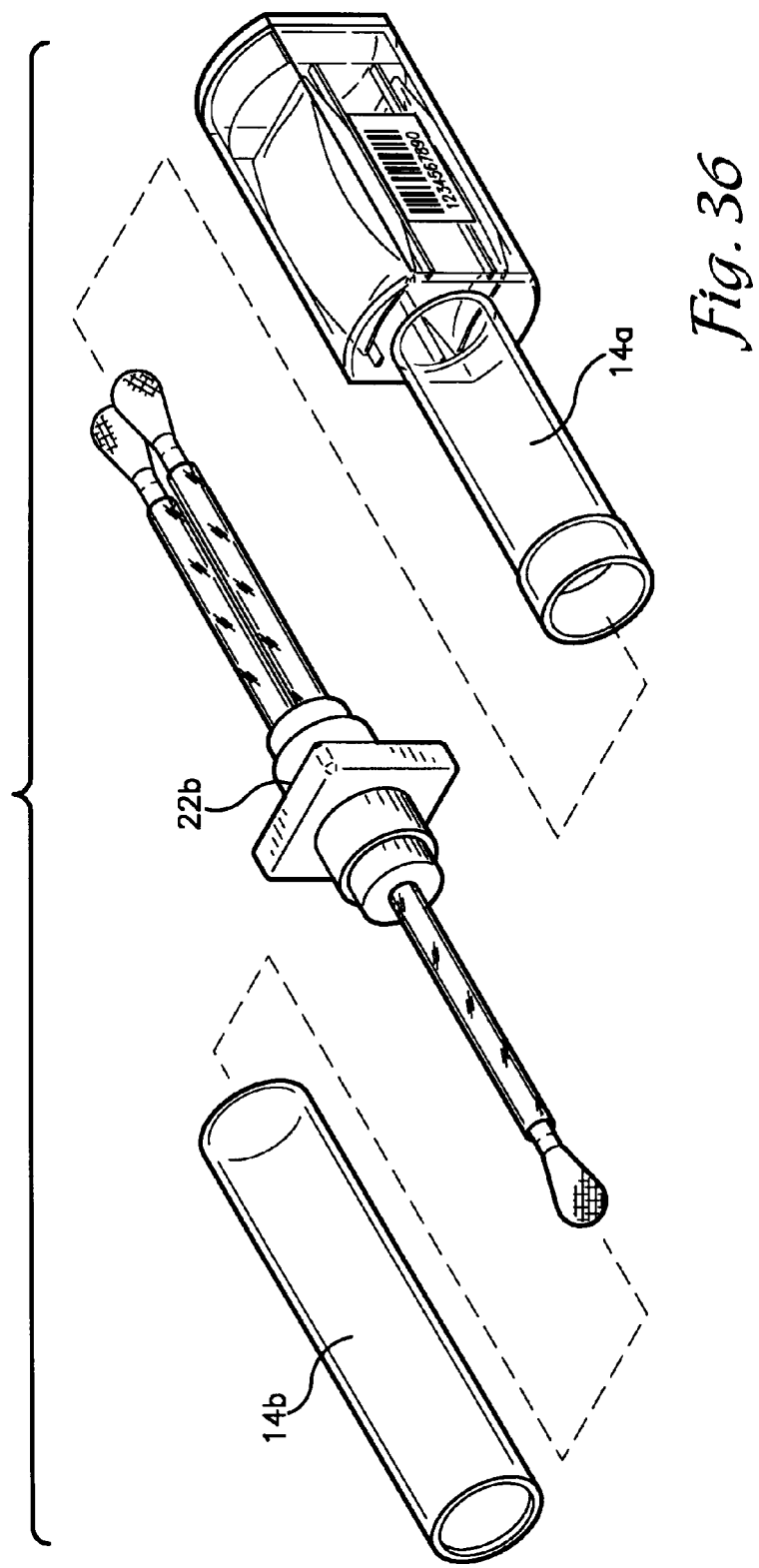
Figure 37:
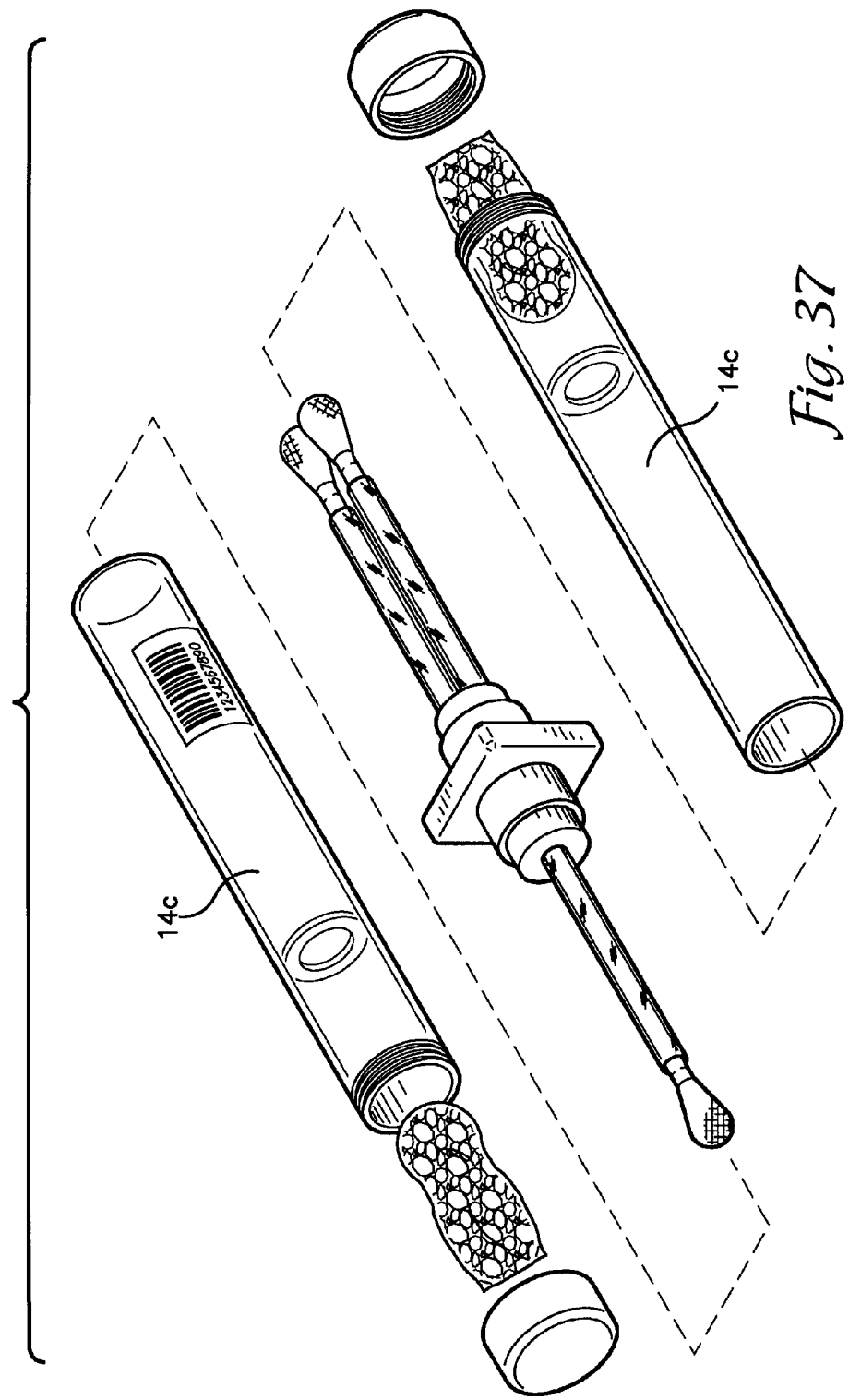

FIG. 34 shows an embodiment having dual specimen collectors 12 positioned into cap 22 for collection of a specimen while using both the wet technique and the dry technique of collection;

FIG. 35 shows an embodiment of a cap having dual voids therein which permit the positioning and securing of dual swabs within the cap as shown in FIG. 34;

FIG. 36 shows an embodiment having a cap embodiment provided with three voids for insertion of swab shafts 16a therein with a single void on one side of cap 22b and two voids on the opposed side of cap 22b; and FIG. 37 shows an exploded view of an embodiment with tubular housings having a desiccant chamber added to the end of the housings 14C.

Figure 38:
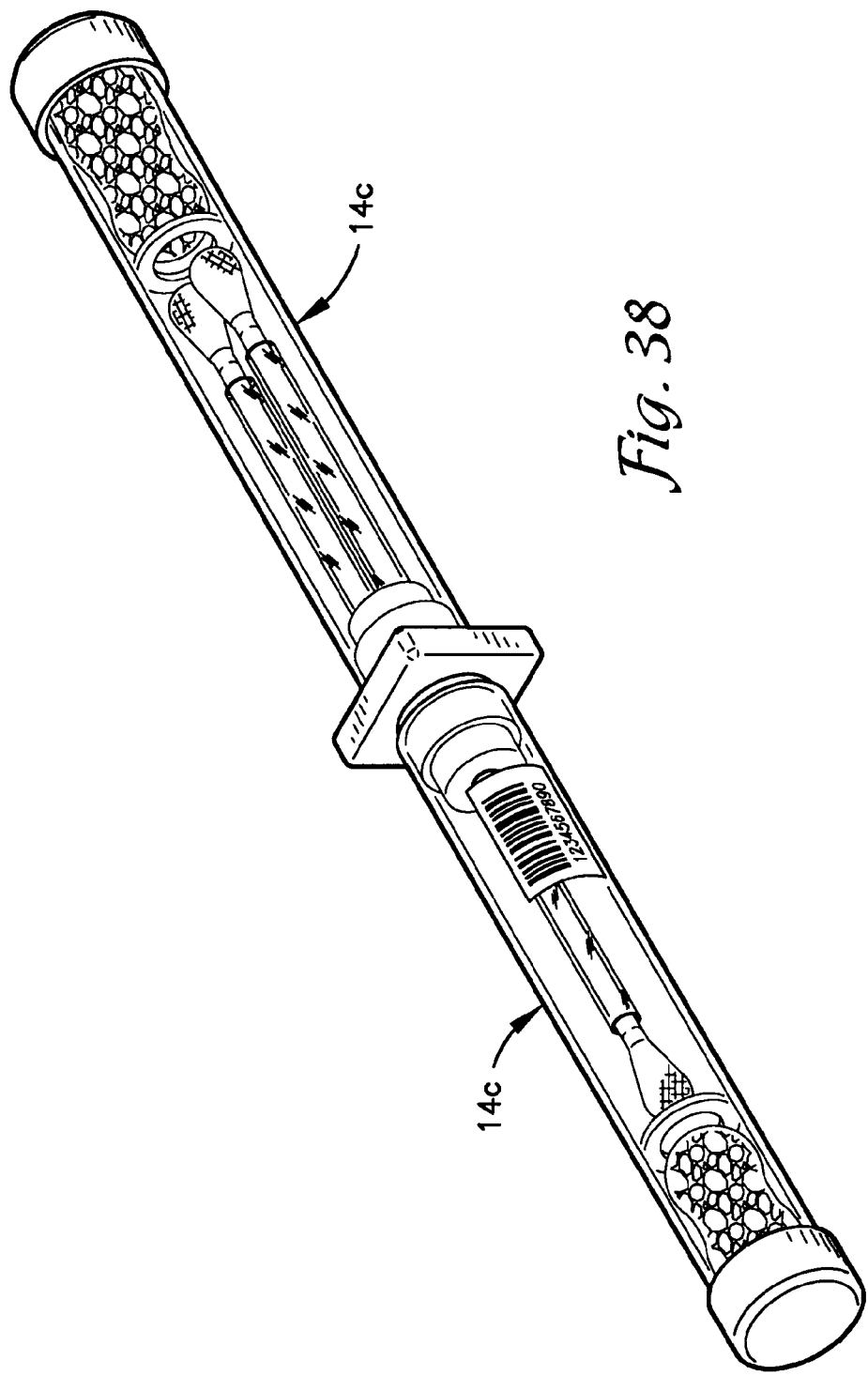

FIG. 38 shows the desiccant-holding housings shown in place on the embodiment shown in FIG. 37.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring now to the drawing figures, the reference numeral 10 generally designates a containerized low pressure sample collection apparatus. The apparatus 10 generally includes a swab assembly 11 (FIG. 3) which extends through a housing structure 18 which may function as a handle to manipulate the apparatus 10.

Referring to FIGS. 1-4, the illustrated swab assembly 11 includes an elongated tubular shaft 22 having a vacuum connection 20 at a vacuum connection end thereof and an absorbent swab member 14 secured to a swab end of the shaft 22. The shaft 22 extends through the housing structure 18 and is secured thereto, as by friction, an adhesive, welding, or the like. The illustrated housing 18 has sections of reduced cross-section at its ends to form plug members 19 to receive a cap member 16 on either end of the housing. The cap 16 may be placed on the vacuum connection end for storage of the cap, as shown within a sealable bag or container 12 in FIG. 1, or on a swab end of he housing 18 to protect the swab member 14, as shown in FIG. 4. The cap member 16 may be provided with an opening or aperture 30 in a side wall or an end wall to admit air for drying the swab member 14 when enclosed therein. The apparatus 10 may be provided with a push-off barrel 28 (FIG. 3) which is coaxially mounted on the shaft 22 between the housing 18 and the swab member 14. The barrel 28 may be pushed against the swab member 14 to separate it from the shaft 22 without otherwise touching the swab to prevent contamination of a sample thereon.

The swab member 14 may be provided in various forms and of various materials depending on the suspected identity and the character of the material to be sampled. The sampled material may be a liquid, a liquid with suspended solids, a gel or a grease, a particulate or granular material, a flaked material, and so forth. Thus, the swab member 14 may be formed of a fibrous material, such as cotton, cellulose, rayon, polyester, or the like, various kinds of sponge or porous materials, a fabric, a paper, a netting material, or the like. The swab member 14 may be in a sterile condition or it may be coated or impregnated with a chemical to attract or bind with a particular substance or coated to prevent migration of the sampled material too deeply into the swab member 14.

The vacuum connection 20 provides for the connection of a portable, low pressure vacuum unit (not shown) thereto to cause an air flow through the swab member 14 into the tubular shaft 22. Such an air flow can facilitate collection of certain kinds of materials within the swab member 14. Alternatively, the apparatus 10 can be used without such a vacuum source.

To establish and maintain a chain of custody of a sample collected using the apparatus 10, it may be marked with identification indicia which is unique to the particular apparatus 10. As illustrated, the housing 18 is marked with indicia 24, such as a barcode. Alternatively, such indicia 24 could be in the form of an alphanumeric serial number. However, an advantage of a barcode is that it can be quickly and accurately scanned, while a serial number is vulnerable to copying errors and transposition of characters. Preferably, no two apparatus 10 have the same indicia 24 so than once the indicia 24 of an apparatus 10 is recorded and associated with a particular case, another apparatus 10 cannot be substituted for the recorded one. The apparatus 10 may be provided with a writable surface 26 to record short notes, such as the initials of the investigator or technician, a time or date, a case number, or the like. The writable surface 26 may be provided as a paper tag adhered to the surface of the housing 18. The apparatus 10 may also be provided with a tamper indicator 32, such as an adhesive seal adhered to the housing 18 and the cap 16 after a sample is collected on the swab member 14.

The identifying indicia 24 may be a unique indicia that is assigned to the collector 10 at the time of manufacture of the collector 10. The unique indicia 24 is intended to be sufficient to distinguish any one collector 10 from all other such collectors ever manufactured. The importance of providing such a unique indicia 24 is that the collector 10 is to be used at a crime scene and may be photographed being used at the crime scene during the evidence collection process (See, FIG. 10), the photographing thus serving to verify the use and association of one particular, unique collector 10 in the collection of evidence at the crime scene. Having a particular indicia uniquely assigned to one and only one device 10 is necessary to provide confirmation that substitute devices were not, and could not have been introduced into the evidence gathering. This uniqueness of identification of device 10 makes concrete the chain of custody of the crime evidence collected on the device 10 and is necessary to eliminate claims that a mix-up in devices 10 or a substitution of devices 10 having the same identification indicia may have occurred thereby invalidating the evidence collection. In this manner, a law enforcement agency can ensure and demonstrate that a device 10 presenting a particular unique indicia that appears in a photograph taken at a crime scene is the only such device in existence, and that no second device 10 that by chance has the same identification number has been inadvertently substituted for the particular device 10 actually used and photographed at the crime scene to collect the evidence being submitted in a prosecution.

Figure 8:
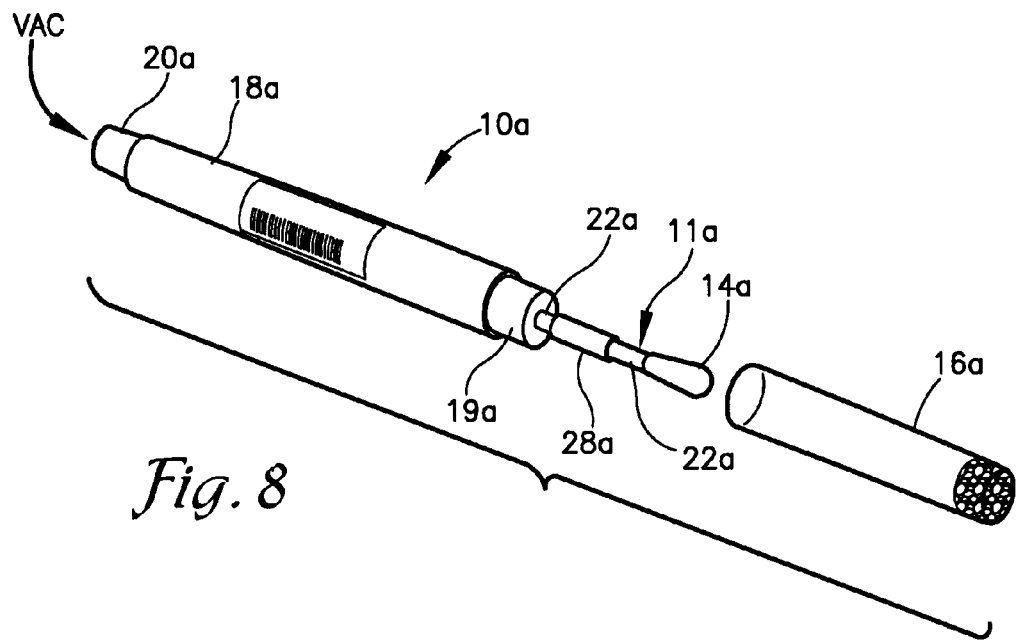
FIG. 8 is a perspective view of a modified embodiment of the sample collection apparatus which has a cylindrical cross section, shown with a cap removed to expose a vacuum connection and with the cap positioned to be placed over a swab member thereof.
Figure 9:
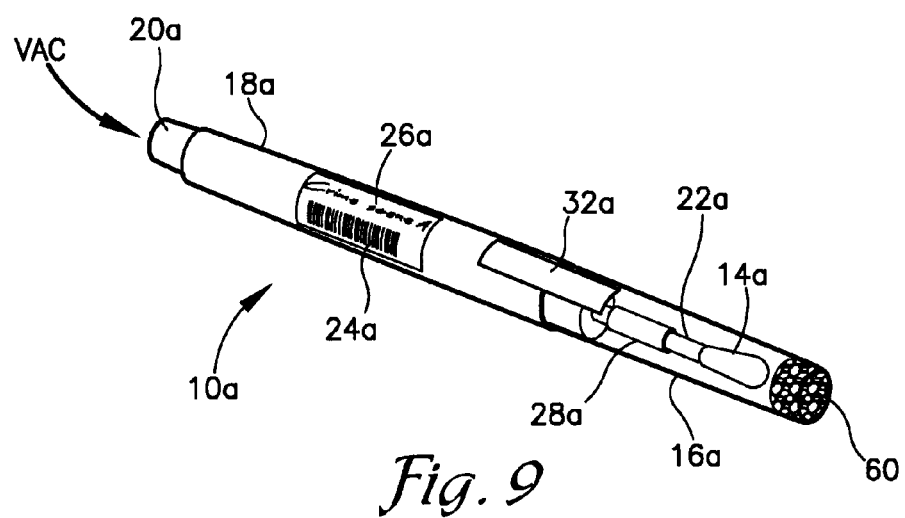
FIG. 9 is a perspective view of the cylindrical sample collection apparatus, shown with the cap in covering relation to the swab and diagrammatically showing a desiccant positioned in the cap.

The apparatus 10 is illustrated in FIGS. 1-4 with a housing 18 having a substantially square cross-sectional shape. Alternatively, the housing 18 could have other non-round cross-sectional shapes, such as rectangular, triangular, elliptical, or the like. FIGS. 8 and 9 illustrate a modified embodiment 10a of the containerized low pressure sample collection apparatus. The apparatus 10a includes a swab assembly 11a formed by an elongated tubular shaft 22a extending through a housing structure 18a and terminating at a vacuum connection end with a vacuum connection 20a. The illustrated housing 18a has a circular cross-sectional shape and is, thus, cylindrical. At an end opposite the vacuum connection 20a, a swab member 14a is secured to the shaft 22a. The housing structure 18a may be used as a handle for manipulating the apparatus 10a to collect a sample of a substance on the swab member 14a. The housing 18a may be provided with a section of reduced diameter which forms a plug member 19a to receive the open end of a cap member 16a to cover the swab member 14 after a sample has been collected. The illustrated vacuum connection 20a may also be sized to receive the end of the cap 16a for storage thereof. The vacuum connection 20a provides for connection of a low pressure vacuum unit (not shown) to draw air through the swab member 14a to facilitate collection of samples of certain kinds of materials. Alternatively, the apparatus 10a may be used for collection of other types of materials without the use of such a vacuum unit.

As shown in FIG. 9, a tamper seal 32a may be provided to adhere to the housing 18a and the cap 16a to show visible signs of attempts to remove the cap 16a. The housing 18a may be provided with identification indicia 24a, such as a barcode which uniquely identifies the apparatus 10a. The housing 18a may, further, be provided with a writable area 26a to receive written notes pertaining to the sample collected. The illustrated apparatus 10a has a push-off barrel 28a positioned on the shaft 22a between the housing 18a and the swab member 14a for use in pushing the swab member 14a off the end of the shaft 22a. The cap 16a may have a quantity of a desiccant material 60 positioned therein to facilitate drying of the swab member 14a when covered by the cap 16a. Alternatively, the cap 16a may be provided with an opening (not shown) similar to the opening 30 in the cap 16 of FIGS. 1-4. It should be noted that the cap 16 in FIGS. 3 and 4 could also be provided with a desiccant material 60 to promote drying of the swab member 14.

FIGS. 5-7 illustrate a slide-out embodiment 10b of the containerized low pressure sample collection apparatus. The apparatus 10b includes a swab assembly 11b which is slidably supported by a hollow or tubular housing 40, which forms an enclosure for a swab member 14b or which can function as a handle for manipulating the apparatus 10b to collect a sample. The swab assembly 11b includes an elongated tubular shaft 22b having a vacuum connection 20b at a vacuum connection end and the swab member 14b secured at an opposite swab end. The swab assembly 11b includes a swab support and centering structure 50 formed by panels 52 and 54 and additional box structure members (not shown) within the housing 40. The swab assembly 10b may include a push-off barrel 28b telescoped onto the shaft 22b between the support structure 50 and the swab member 14b for use in separating the swab member 14b from the shaft 22b. The swab member 14b, the support structure 50, the portion of the shaft 22b therebetween, and the barrel 28b, if present, form a sample collection head 46 of the swab assembly 11b. The vacuum connection 20b allows a portable low pressure vacuum source (not shown) to be connected to the apparatus 10b to establish an air flow through the swab member 14b and the shaft 22b to facilitate collection of some types of samples. Alternatively, the apparatus 10b may be used without such a vacuum source.

The illustrated housing 40 is an elongated structure with a square cross-section through which the swab assembly 11b extends. At a swab end 42 (FIG. 5) toward the swab member 14b, the housing 40 has a pair of flaps 48a and 48b which cooperate to close the swab end of the housing 40. The housing 40 may be formed from a material such as a stiff paper, a plastic, or a composite of sheet materials. The apparatus 10 may be provided in a sealable bag or container 12b and may be replaced in the bag 12b after use.

The sample collection apparatus 10b would typically be provided in the bag 12b with the sample collection head 46 retracted within the housing 40 and the flaps 48a and 48b closed to prevent contamination of the swab member 14b. For use in the field to collect a sample of a substance, the apparatus 10b is removed from the bag 12b, the portion of the shaft 22b near the vacuum connection 20b is grasped in one hand 44, the housing 40 grasped in the other hand, and the swab assembly 11b advanced in the direction of arrow A (FIG. 6) to extend the sample collection head 46 out of the housing 40 through the flaps 48a and 48b. A source of vacuum can be connected to the vacuum connection 20b if suitable. The housing 40 may be used as a handle to manipulate the apparatus 10b in collecting the sample.

After the sample is collected, the vacuum connection end of the swab assembly 11b is again grasped and pulled in the direction of arrow B (FIG. 7) to retract the sample collection head 46 within the housing 40 for protection against contamination of the sample. The flaps 48a and 48b can then be closed. It is foreseen that a tamper seal, similar to the tamper seal 32 of FIG. 4, could be adhesively applied to the flaps 48a and 48b to indicate any attempt to access the swab member 14b prior to official analysis. The swab support and centering structure 50 retains the swab member 14b out of contact with the walls of the housing 40 when the swab member 14b is positioned within the housing 40. After the swab assembly 11b is retracted and the flaps 48a and 48b closed, the apparatus 10b may be replaced in the bag 12b for transport to a laboratory for analysis of the sample collected. It will be appreciated by those skilled in the art that after a liquid specimen has been collected on swab member 14b that drying of the liquid specimen is preferred. In the present embodiment swab support and centering structure 50 retains the swab member 14b in an elevated position while collection apparatus 10b is resting on a surface thereby avoiding cross-contamination of swab member 14b and the specimen collected thereon.

The illustrated housing 40 is with identifying indicia 24b, such as a barcode, to uniquely identify the sample collection apparatus 10b. Alternatively, other types of identifying indicia could be provided, such as a serial number or the like. The housing 40 may also be provide with a writable surface 26b to allow an investigator or technician to record selected notes on the housing 40.

Figure 10:
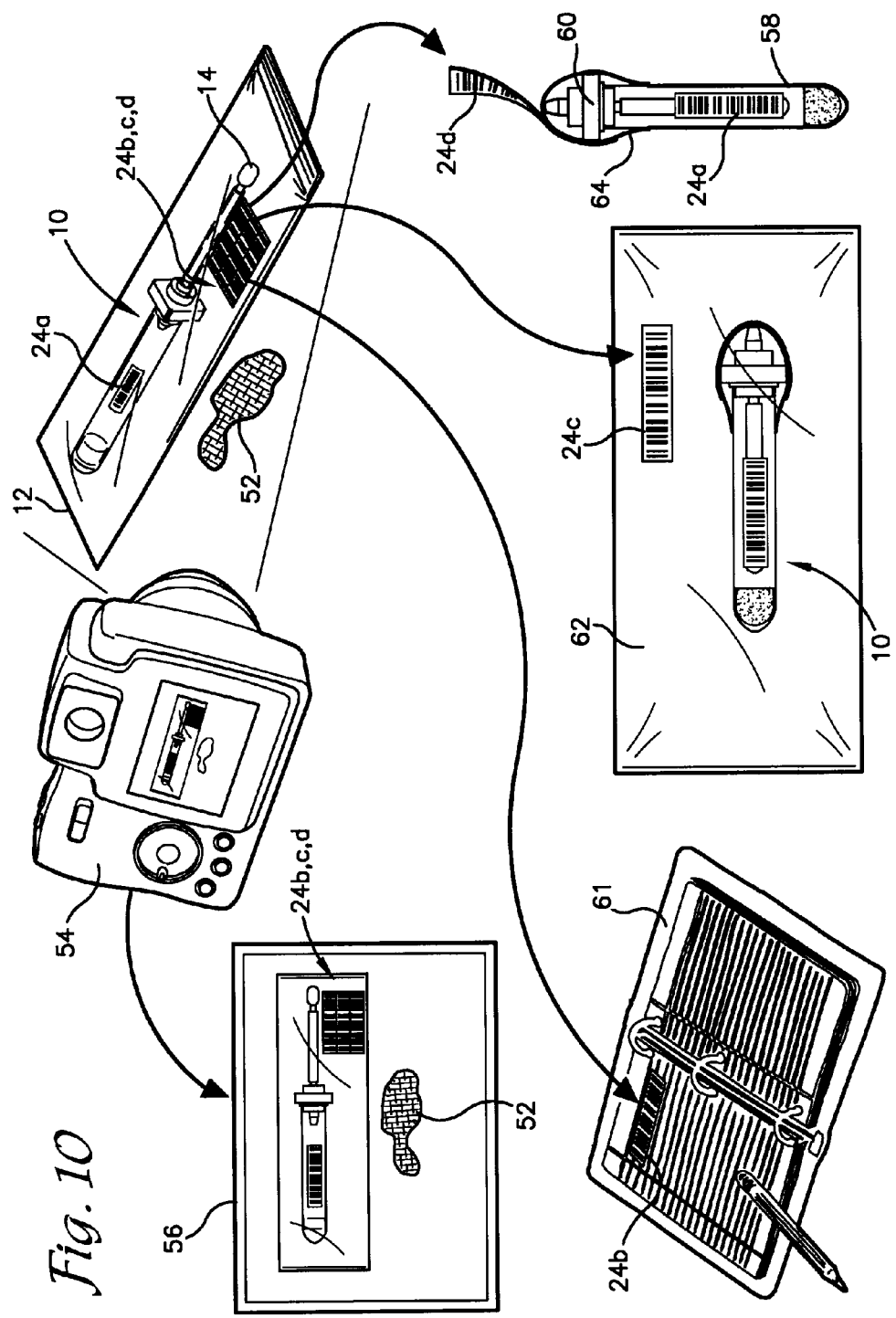
FIG. 10 shows a schematic representation of method steps related to a crime scene method of investigation in which a collector within a clear plastic bag and having a unique indicia thereon and additional copies of the unique indicia on the bag placed next to a crime specimen to be sampled and showing photographic recording of the juxtaposition between the sample and the unopened bag and showing the photograph recording the juxtaposition and the relevant barcodes with additional representation showing the barcodes transferred from the bag to a crime investigator's notebook and to a transportation bag for shipping the collector having a specimen collected thereon and showing a copy of the unique barcode indicia applied to a tamper-proof tape that has been applied to the specimen collector after collecting the sample and sealing the absorbent collector into the housing or tube of the collector.

Referring now to FIG. 10, the method of forensic specimen collection while maintaining a chain of custody, will be described. As previously described, it is important for a law enforcement agency to ensure and demonstrate that any specimen collection device 10 has been properly maintained within police custody and that tampering with the specimen has been prevented or that any attempt to tamper with the specimen would be indicated by some type of physical modification of the specimen or the container within which the specimen is held. Further, in maintaining the chain of custody of crime scene evidence and providing sufficient proof that laboratory analyses were performed on a particular specimen actually obtained from a crime scene, it is necessary to document the entire collection process, transportation process, analysis process and reporting of results for any crime scene specimen that is collected. The present apparatus may be used in a method of evidence collection which, by the structure of the apparatus, permits use of a method which serves to maintain the chain of custody of crime scene evidence and to assist in the documentation of the collection and analysis of the evidence.

Still referring to FIG. 10, a crime scene specimen 52, is shown which may be a fluid such as blood or saliva, or the specimen 52 may be a solid which has dried at a crime scene or the specimen 52 may be any other unknown piece of evidence which is collectable by contacting the specimen 52 with a swab member 14, such as that shown attached to collector 10.

In the method of evidence collection, a crime scene investigator places sealable bag or container 12 having apparatus 10 therein adjacent a crime scene specimen 52. The investigator then uses a camera 54 to photograph the unopened sealable bag 12 having apparatus 10 inside adjacent a crime scene sample specimen 52. The result of this step is that a photograph 56 is generated which documents the particular specimen 52 to be collected adjacent the collector 10 still sealed with bag 12 and bearing unique indicia 24a on collector 10 and indicia 24b,c,d in place on the bag. This serves to verify that prior to collection, container 10 was in bag 12 and in good condition and that bag 12 had not been opened to allow prior access container 10 and swab 14.

The step of sample collection is shown in FIG. 11, wherein container 10 has been removed from bag 12 (FIG. 10) and swab member 14 is applied to specimen 52, such that a portion specimen 52 adheres to swab member 14. Once the portion of specimen 52 has been collected on swab member 14, the swab member 14 is inserted into container 58 and swab member 14 is sealed within container 58 by the frictional fit between container 58 and cap 60. It will be appreciated that indicia 24a continues to be present on container 58 to maintain the particular, unique identity of container 58.

Again referring to FIG. 10, it may be desirable for the crime scene investigator to record various observations and notations regarding specimen 52 and the manner of collection of specimen 52 in a notebook 61. To allow the crime scene investigator to cross-reference, specimen 52 and collector 10, with the notes taken in notebook 61, a second copy of unique indicia 24, in this case, 24b, is removed from bag 12 and applied to notebook 61. It will be appreciated that indicia 24a is adhered at the time of manufacture to container 10 and indicia 24b,c,d are adhered to the outside of or inside of bag 12 at the time of manufacture. Once the crime scene investigator has photographed bag 12 and container 10 adjacent to specimen 52, and has recorded the investigator's observations in notebook 61, it is then necessary to transport the container 58 having swab member 14 therein to a laboratory for analysis. This is accomplished by placing collector 10 into a transportation bag 62 to which a third copy of unique indicia 24, in this case unique indicia 24c, is applied to the outside or to the inside of bag 62. Container 10, having been inserted into bag 62 is then sealed within bag 62 such that access to container 10 can only be achieved by some degree of physical destruction of bag 62. Prior to inserting container 10 into bag 62, it is good practice to apply an additional seal to container 58 once cap 60 has been inserted to close container 58. This additional seal is typically in the form of a tape seal such as tamper-proof tape 64, which has been applied to container 58 and to cap 60. It will be appreciated by those skilled in the art that once the tamper-proof tape has been applied to container 58 and cap 60, that entry into tube 58 can only be achieved by the physical destruction of tamper-proof tape 64. To particularly identify tamper-proof tape 64 that has been applied by the investigator at a crime scene, a fourth copy of indicia 24, in this case indicia 24d, is adhered to tamper-proof tape 64. In this manner, the destruction of tamper-proof tape 64, also would involve destruction of unique indicia 24d, which would demonstrate tampering with the container 58 and potentially the sample within on swab member 14. It further will be appreciated that an individual attempting to substitute a new tamper-proof seal for the tamper-proof seal 64 applied by the investigator, would be frustrated by the lack of a copy of unique indicia 24d to apply to the substituted tamper-proof seal 64. This may be the case where the adhesive used to apply unique indicia 24d to tamper-proof 64 is a non-releasable adhesive and the separation of any of unique indicia 24a,b,c,d from the object to which they applied after removal from bag 12, will result in the destruction of the unique indicia thus preventing substitution of the indicia 24a,b,c,d onto an alternate item.

Therefore, as described, it will be appreciated that the method taught herein provides a complete, verifiable, chain of custody which begins at the time just prior to collection of a specimen and continues to the time at which the specimen is received at the laboratory for analysis, while further extending to provide verification of investigator notes in a crime notebook and additional identification and verification of tamper-proof tape used to seal the specimen collector. It further will be appreciated that as unique indicia 24 is intended to be a one, and only one use identifier, that the particular crime scene at which collector 10 is used, will be uniquely identifiable from all other crime scenes and that any notes taken by an investigator in notebook 60, will also be uniquely identifiable in addition to the maintenance to the chain of custody as taught by the maintenance of the chain of custody as taught by the present method.

Referring now to FIGS. 13, 14, and 15, an additional embodiment will be described. The embodiment of FIGS. 13, 14, and 15 permits ease of separation of swab member 14 from collector 10 and in particular, the separation of swab member 14 from shaft 22 to allow swab 14 alone to be inserted into a container or vial for storage or analysis or elution of the material collected on swab 14. The ease of separation previously described is achieved by inclusion of a score line 70 on shaft 22. This score line 70, or line of weakness or shaft of fracturable material, permits snapping or breaking of shaft 22 at the point of score line or point of weakness 70. This function is shown in use in FIG. 14 wherein swab 14 is introduced into a vial 72 and by firmly biasing swab 14 against the wall of vial 72, shaft 22 may be caused to break along score line 70, thereby releasing swab 14 from shaft 22 and allowing the depositing of swab 14 within vial 72 as shown in FIG. 15. It will be appreciated that for maintenance of the chain of custody, that barcode 24a may be made transferable thereby permitting transfer of barcode 24a unto vial 72 to thereby maintain the identification of vial 72 and swab 14 contained therein. It will be appreciated by those skilled in the art, that such transfer of indicia 24a is not in keeping with the previously described method of chain of custody, and that this particular embodiment is not intended to detract from the previously described chain of custody.

Referring now to drawing FIGS. 16-29, the reference numeral 10 generally designates a low pressure sample collection apparatus. The apparatus 10 generally includes a swab assembly 11 and a container member 12. As will be described below, the swab assembly 11 can be engaged with the container 12 in such a manner as to use the container 12 as a handle or as an enclosure to protect the swab assembly 11.

Figure 16:
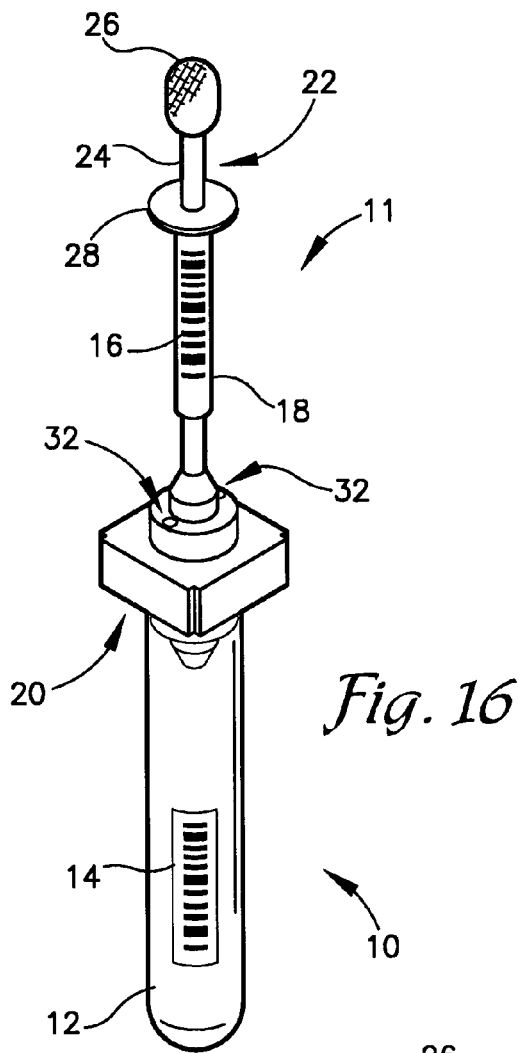
FIG. 16 is a perspective view of an embodiment of a low pressure sample collection apparatus, shown with an embodiment of a container member plugged onto a cap member for use of the container member as a handle.
Figure 17:
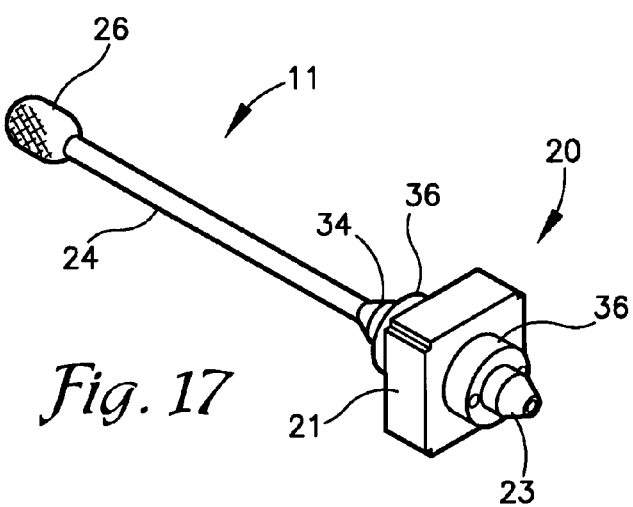
FIG. 17 is a perspective view of the sample collection apparatus with the container member removed.
Figure 20:
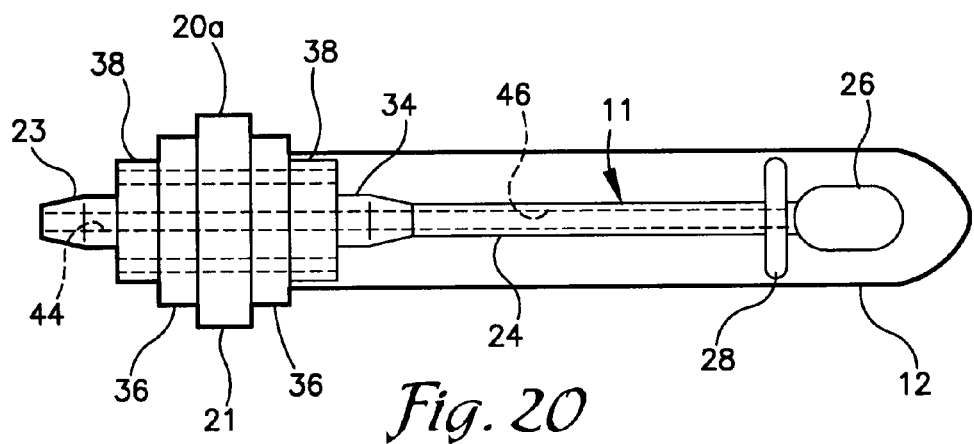
FIG. 20 is an enlarged side elevational view of a modified embodiment of the sample collection apparatus including a cap member having plug members of varying diameters to enable plugging the cap into a variety of sizes of containers or other receptacles.

Referring to FIG. 16, the swab assembly 11 includes a cap member 20 having a tubular shaft 24 extending from one side thereof from a shaft connection portion 34 (FIG. 17). An absorbent or swab member 26 is secured to an outer end of the shaft 24 to form a sample collection head 22. The cap member 20 includes a central cap portion 21 with stopper or plug members 36 extending from opposite sides thereof. One of the plug members 36 has the shaft connection portion 34 extending therefrom. The opposite plug member 36 has a vacuum connection or nipple 23 extending therefrom. The illustrated central cap portion 21 has a square cross section which prevents the swab assembly 11 from rolling if the assembly should be placed on a surface. The plug members 36 have the same diameter so that either plug member 36 can be inserted into the end of the container 12. The illustrated container member 12 has an open mouth at one end and is closed at an opposite end. The cap member 20 may have passages or bores 32 formed through the plug members 36 to enable drying air to enter the container 12 when the collection head 22 is positioned therein, as shown in FIG. 20, to dry the swab member 26. As shown in FIG. 16 two bores 32 are present in a preferred embodiment to assist air circulation into the tube for drying of the specimen on the collection head 22.

Referring to FIG. 16, a push-off barrel 18 is co-axially mounted onto the shaft 24 and is slidable thereon. The barrel 18 can be used to push the swab member 26 off the shaft 24, as for analysis, without touching and possibly contaminating a sample on the swab member 26. Additionally, the swab assembly 11 may be provided with a drying disk 28 encircling the shaft 24. The disk 28 has a diameter sufficient to prevent contact of the swab member 26 with a resting surface if the swab assembly 11 is placed on such a surface to dry. The disk 28 may be of a flat circular construction or of a fatter doughnut-shaped configuration.

In order to establish a chain of custody of any evidence sample taken with the apparatus 10, it is necessary to associate the sample with the investigating officer or an investigating technician and with the scene where the sample was taken. In order to facilitate establishing such a chain of custody, the illustrated apparatus 10 is preferably marked with identifying indicia, such as indicia 14 applied to the container 12 and indicia 16 applied to the swab assembly 11, such as on the barrel 18. Such indicia 14 and 16 may be in the form barcodes, as illustrated, serial numbers, or the like. Preferably, the indicia 14 and 16 are identical so that a swab assembly 11 can be matched with a container 12. Since barcodes are typically read by laser scanning devices, it may be easier to scan the container barcode 14 when the swab assembly 11 is positioned within the container 12. Preferably, each indicia set 14, 16 is unique to a particular sample collection apparatus 10 so that no two apparatus 10 have the same indicia set. This prevents the substitution of evidence for evidence that was originally collected at a scene. Alternatively, other means of marking components of the apparatus 10 for identification are foreseen, such as the provision of tags (not shown) having writable surfaces. Additionally, it is foreseen that some form of tamper seal could be applied to the apparatus 10, such as an adhesive tamper seal (not shown) adhered to the cap member 20 and container 12 after the swab assembly 11 is positioned within the container 12 to show if the cap member 20 has been removed from the container 12. In addition cap member 20, or some portion thereof, may be provided with a color code so that a particular color of cap member 20 is used for the collection of a particular type of evidence specimen. For example a red colored cap member 20 may be used for the collection of a blood evidence sample while a blue cap member 20 may be used for the collection of an evidence sample of unknown material.

Figure 18:
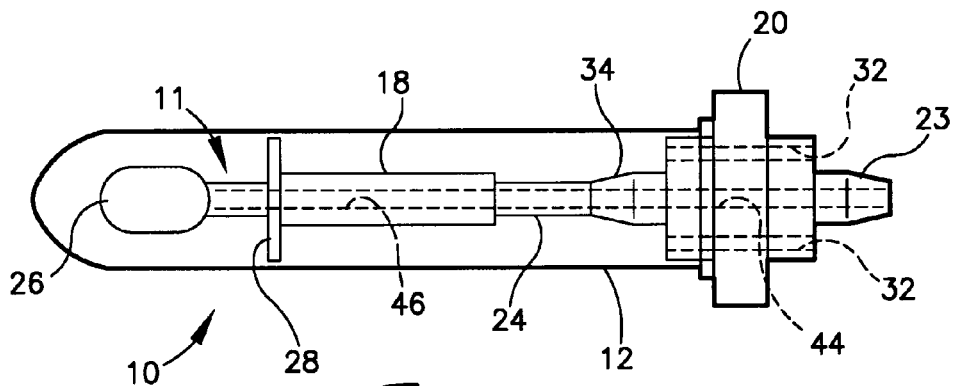
FIG. 18 is an enlarged side elevational view of the sample collection apparatus of FIG. 16, showing the container member plugged onto the cap member to enclose a swab member within the container and with push-off barrel and a drying disk adjacent the swab member.
Figure 19:
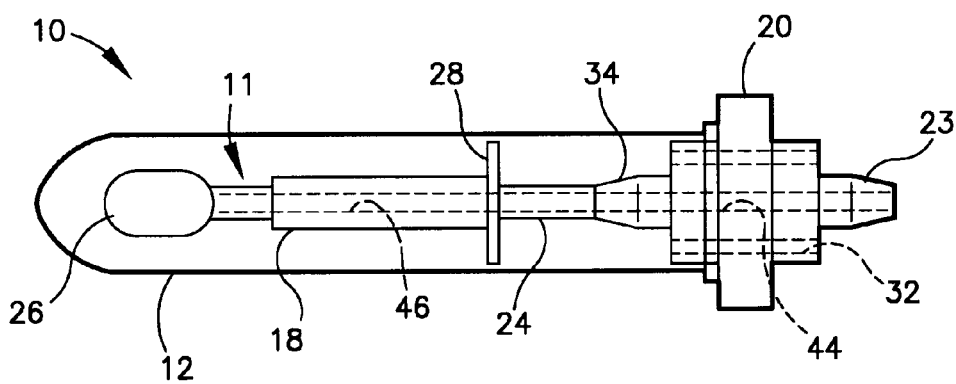
FIG. 19 is a view similar to FIG. 18 and showing the drying disk of the sample collection apparatus positioned adjacent the cap member.

FIG. 16 shows the sample assembly 11 extending from the container member 12 so that the container 12 can be used as a handle to facilitate manipulation of the apparatus 10 to collect a substance sample. FIG. 18 shows the swab assembly 11 positioned within the container 12. In FIG. 18, the drying disk 28 is positioned between the barrel 18 and the swab member 26. Alternatively, the drying disk 28 could be positioned between the barrel 18 and the connection portion 34 of the cap member 20, as shown in FIG. 19. The drying disk 28 can also function as a centering disk to prevent the swab member 26 from contacting inner surfaces of the container 12 when positioned therein. As shown in FIGS. 18 and 19, an airflow passage 46 extends through the shaft 24 and communicates with a passage 44 through the cap member 20, including the connection portion 34 of the cap 20, the plug portions 36, the central cap portion 21, and the nipple 23.

FIG. 20 shows the sample collection apparatus 10 with a modified cap member 20a. The cap member 20a includes a central portion 21 with plug members 36 extending from opposite sides thereof. Additionally, the cap 20a includes a second set of plug members 38 extending from outer surfaces of the plug members 36. As illustrated, the plug members 38 have a smaller diameter than the plug members 36 to enable them to be inserted into containers or other devices, such as laboratory equipment having different diameters. The nipple 23 and shaft connection portion 34 extend from opposite outer surfaces of the plug members 38. The modified cap member 20a includes the passage 44 which communicates with the passage 46 within the shaft 24.

Figure 21:
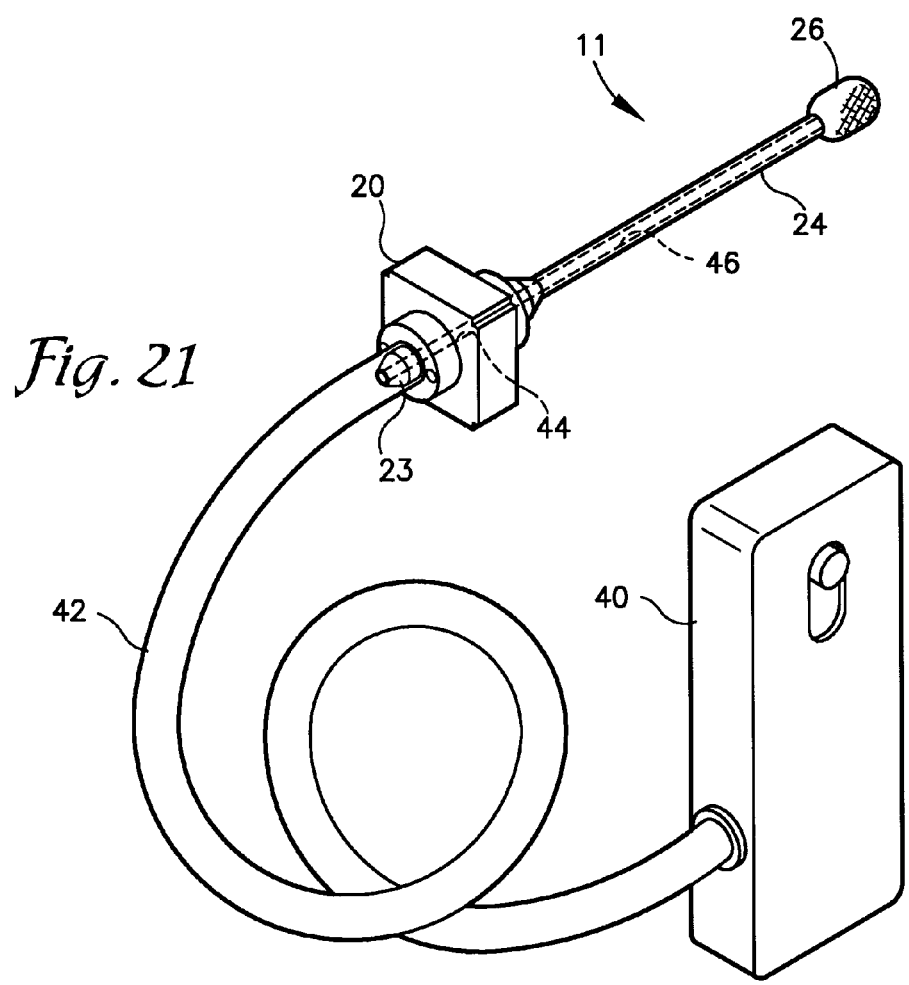
FIG. 21 is a perspective view of the sample collection apparatus, shown with a low pressure vacuum source connected thereto.

Referring now to FIG. 21, an additional aspect is shown which comprises the use of a suction device and method of sample collection. The suction for the sample collection is provided by a portable vacuum device or source 40 which is attached by vacuum hose 42 to the nipple 23 of the cap 20. In this embodiment, a passageway 44 is provided through cap 20. This passage 44 in cap 20 communicates with passage 46 within the shaft 24, which extends to within the swab member 26 The vacuum device 40 is activated to draw air through the swab member 26 to collect particles of a substance within the swab member 26 for later analysis. After collection of a sample, the hose 42 may be disconnected from the nipple 23 and the swab assembly 11 placed within a container 12 to prevent contamination or dilution of the sample. The vacuum device 40 preferably draws air at a relatively low pressure to avoid contaminating the sample with extraneous materials during collection. To further assist in the release of specimen from the swab member 26, the swab 26 may be coated with a dissolvable coating such a albumin or other suitable coating medium. The attracted specimen particles may then be released from the surface of swab member 26 when the dissolvable coating is put into solution.

Referring now to drawing FIGS. 16-29, the reference numeral 70 generally designates a low pressure sample collection apparatus. The apparatus 70 generally includes a swab assembly 71 and a container member 72. As will be described below, the swab assembly 71 can be engaged with the container 72 in such a manner as to use the container 72 as a handle or as an enclosure to protect the swab assembly 71.

Figure 22:
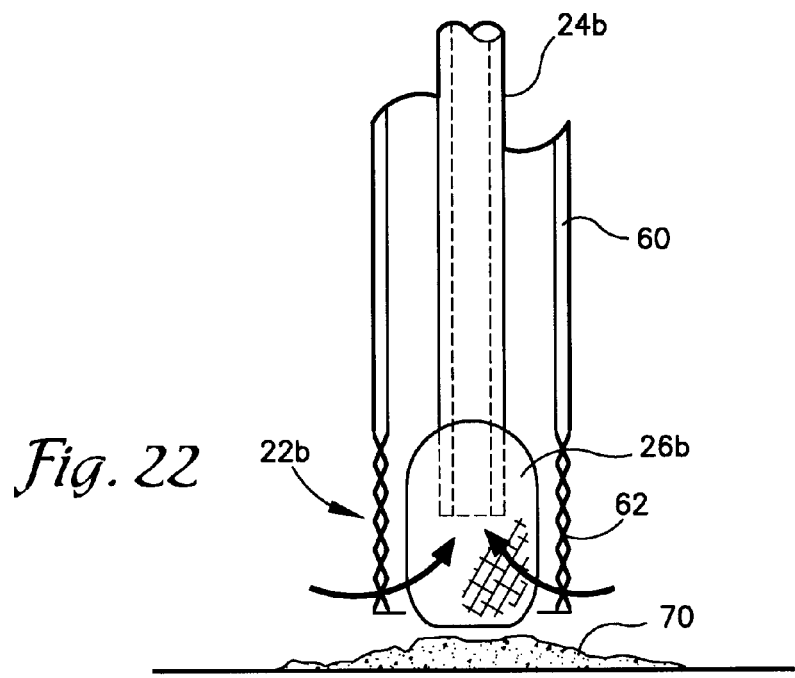
FIG. 22 is an enlarged fragmentary cross-sectional view of a second modified embodiment of the sample collection apparatus which includes a cylindrical swab casing with a porous region in the vicinity of the swab member to control the flow of air about the swab member.

Referring to FIG. 16, the swab assembly 71 includes a cap member 80 having a tubular shaft 84 extending from one side thereof from a shaft connection portion 94 (FIG. 22). An absorbent or swab member 86 is secured to an outer end of the shaft 84 to form a sample collection head 82. The cap member 80 includes a central cap portion 81 with stopper or plug members 96 extending from opposite sides thereof. One of the plug members 96 has the shaft connection portion 94 extending therefrom. The opposite plug member 96 has a vacuum connection or nipple 83 extending therefrom. The illustrated central cap portion 81 has a square cross section which prevents the swab assembly 71 from rolling if the assembly should be placed on a surface. The plug members 96 have the same diameter so that either plug member 96 can be inserted into the end of the container 72. The illustrated container member 72 has an open mouth at one end and is closed at an opposite end. The cap member 80 may have passages or bores 92 formed through the plug members 96 to enable drying air to enter the container 72 when the collection head 82 is positioned therein, as shown in FIG. 20, to dry the swab member 86. As shown in FIG. 16 two bores 92 are present in a preferred embodiment to assist air circulation into the tube for drying of the specimen on the collection head 82.

Referring to FIG. 16, a push-off barrel 78 is co-axially mounted onto the shaft 84 and is slidable thereon. The barrel 78 can be used to push the swab member 86 off the shaft 84, as for analysis, without touching and possibly contaminating a sample on the swab member 86. Additionally, the swab assembly 71 may be provided with a drying disk 88 encircling the shaft 84. The disk 88 has a diameter sufficient to prevent contact of the swab member 86 with a resting surface if the swab assembly 71 is placed on such a surface to dry. The disk 88 may be of a flat circular construction or of a fatter doughnut-shaped configuration.

In order to establish a chain of custody of any evidence sample taken with the apparatus 70, it is necessary to associate the sample with the investigating officer or an investigating technician and with the scene where the sample was taken. In order to facilitate establishing such a chain of custody, the illustrated apparatus 70 is preferably marked with identifying indicia, such as indicia 74 applied to the container 72 and indicia 76 applied to the swab assembly 71, such as on the barrel 78. Such indicia 74 and 76 may be in the form barcodes, as illustrated, serial numbers, or the like. Preferably, the indicia 74 and 76 are identical so that a swab assembly 71 can be matched with a container 72. Since barcodes are typically read by laser scanning devices, it may be easier to scan the container barcode 74 when the swab assembly 71 is positioned within the container 72. Preferably, each indicia set 74, 76 is unique to a particular sample collection apparatus 70 so that no two apparatus 70 have the same indicia set. This prevents the substitution of evidence for evidence that was originally collected at a scene. Alternatively, other means of marking components of the apparatus 70 for identification are foreseen, such as the provision of tags (not shown) having writable surfaces. Additionally, it is foreseen that some form of tamper seal could be applied to the apparatus 70, such as an adhesive tamper seal (not shown) adhered to the cap member 80 and container 72 after the swab assembly 71 is positioned within the container 72 to show if the cap member 80 has been removed from the container 72. In addition cap member 80, or some portion thereof, may be provided with a color code so that a particular color of cap member 80 is used for the collection of a particular type of evidence specimen. For example a red colored cap member 80 may be used for the collection of a blood evidence sample while a blue cap member 80 may be used for the collection of an evidence sample of unknown material.

FIG. 16 shows the swab assembly 71 extending from the container member 72 so that the container 72 can be used as a handle to facilitate manipulation of the apparatus 70 to collect a substance sample. FIG. 18 shows the swab assembly 71 positioned within the container 72. In FIG. 18, the drying disk 88 is positioned between the barrel 78 and the swab member 86. Alternatively, the drying disk 88 could be positioned between the barrel 78 and the connection portion 94 of the cap member 80, as shown in FIG. 19. The drying disk 88 can also function as a centering disk to prevent the swab member 86 from contacting inner surfaces of the container 72 when positioned therein. As shown in FIGS. 18 and 19, an airflow passage 106 extends through the shaft 84 and communicates with a passage 104 through the cap member 80, including the connection portion 94 of the cap 80, the plug portions 96, the central cap portion 81, and the nipple 83.

FIG. 20 shows the sample collection apparatus 70 with a modified cap member 80a. The cap member 80a includes a central portion 81 with plug members 96 extending from opposite sides thereof. Additionally, the cap 80a includes a second set of plug members 98 extending from outer surfaces of the plug members 96. As illustrated, the plug members 98 have a smaller diameter than the plug members 96 to enable them to be inserted into containers or other devices, such as laboratory equipment having different diameters. The nipple 83 and shaft connection portion 94 extend from opposite outer surfaces of the plug members 98. The modified cap member 80a includes the passage 104 which communicates with the passage 106 within the shaft 84.

Referring now to FIG. 21, an additional aspect is shown which comprises the use of a suction device and method of sample collection. The suction for the sample collection is provided by a portable vacuum device or source 100 which is attached by vacuum hose 102 to the nipple 83 of the cap 80. In this embodiment, a passageway 104 is provided through cap 80. This passage 104 in cap 80 communicates with passage 106 within the shaft 84, which extends to within the swab member 86 The vacuum device 100 is activated to draw air through the swab member 86 to collect particles of a substance within the swab member 86 for later analysis. After collection of a sample, the hose 102 may be disconnected from the nipple 83 and the swab assembly 71 placed within a container 72 to prevent contamination or dilution of the sample. The vacuum device 100 preferably draws air at a relatively low pressure to avoid contaminating the sample with extraneous materials during collection. To further assist in the release of specimen from the swab member 86, the swab 86 may be coated with a dissolvable coating such a albumin or other suitable coating medium. The attracted specimen particles may then be released from the surface of swab member 86 when the dissolvable coating is put into solution.

Figure 23:
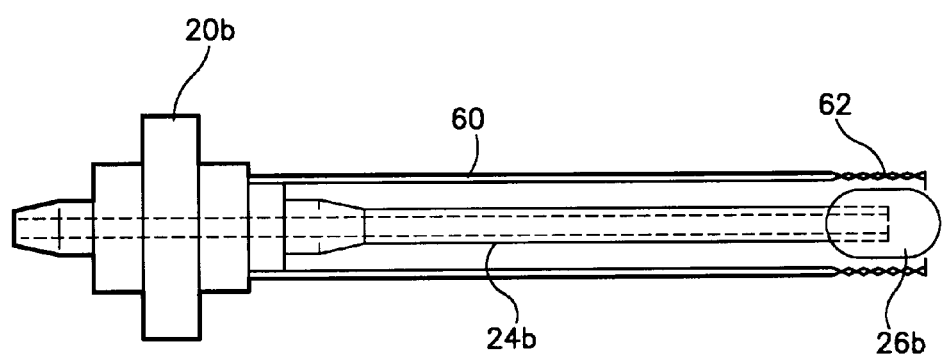
FIG. 23 is a side elevational view of the second modified embodiment of FIG. 22 showing the sample collection apparatus with the casing shown in cross section.

Referring now to FIGS. 22 and 23 an embodiment is shown in which the suction generated by vacuum device 100 travels through cap 80 to provide a reduced pressure atmosphere in a cylindrical casing 120 that coaxially surrounds shaft 84b or collection head 82b. In this manner a low pressure atmosphere, in relation to the general environment outside of casing 120, is provided in casing 120 and to the swab member 86b. Adjacent the swab 86b on casing 120 is a fritted area 122 or an area provided with multiple voids that allow the atmospheric air to enter into casing 120 (FIG. 22). As the air enters voids or fritted area 122 it also draws specimen 130 upwardly onto the swab member 86b. This can be particularly useful where a dried or flaked specimen is located in a cloth or carpet or other woven or porous structure. The casing 120 controls the flow of air about the swab member 86b to focus or confine the area of collection of the specimen 130.

Figure 24:
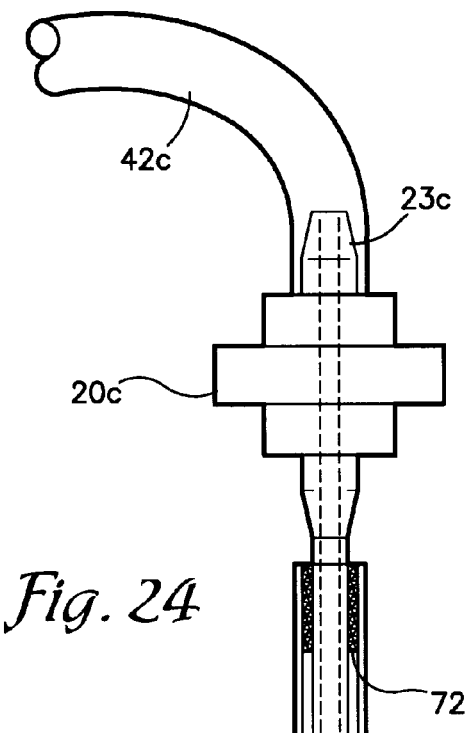
FIG. 24 is a side elevational view of a third modified embodiment of the sample collection apparatus including a slidable swab casing having a cylindrically expanded section adjacent the swab member.

Referring to FIG. 24, an embodiment is shown in which a casing 120 is provided including a cylindrically expanded region 125 surrounding the swab member 86, with the remainder of the casing 120 surrounding at least a portion of the shaft 84. The casing 120 slidably engages the shaft 84 by way of a packing 132, enabling the casing to be slid between a retracted position exposing the swab member 86 and an extended position in which the expanded region 125 surrounds the swab member 86. Similar to the casing 120, the casing 125 controls the flow of air about the swab member 86 to confine the area of sample collection. The illustrated shaft 84 is connected to a cap member 80, to which a vacuum hose 102 is connected by way of the nipple 83. The casing 120 may include a drying or centering disk 88, to enable propping the assembly up for drying of the swab member 86.

Figure 25:
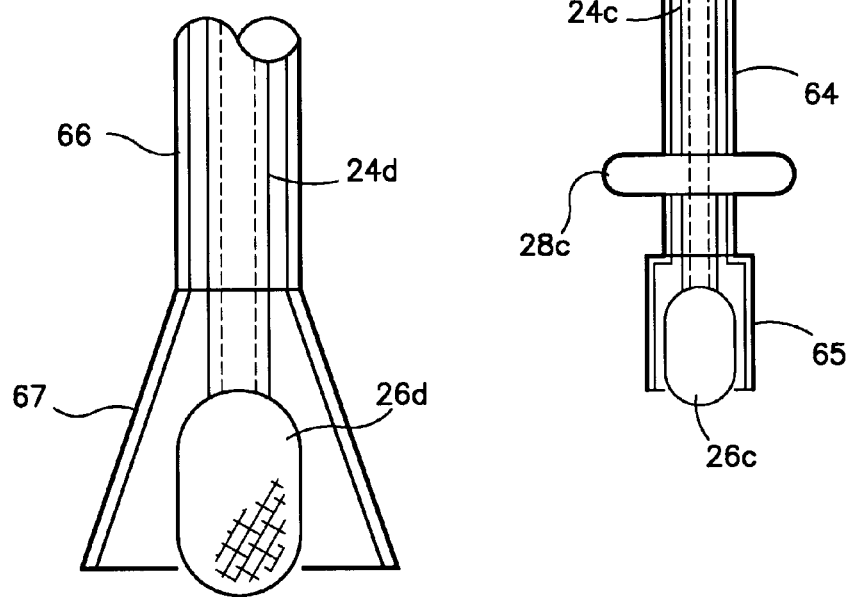
FIG. 25 is an enlarged fragmentary side elevational view a fourth modified embodiment of the sample collection apparatus including a swab casing having a conically expanded section adjacent the swab member.

Referring to FIG. 25, an embodiment is shown in which a casing 120 surrounds a tubular shaft 84 and includes a flared section 127 surrounding a swab member 86. The illustrated flared section 127 is frusto-conical; however, the use of other shapes is foreseen. The casing 120 may be made slidable on the shaft 84 in a manner similar to that shown in FIG. 24. The casing 120 is provided for a similar purpose to the casings 120 and 125; namely to control the flow of air about the swab member 86 to thereby control the area of sample collection.

FIG. 26 is a side elevation view of a fifth modified embodiment 140 of the sample collection apparatus having a secondary chamber 142 included with the casing 144. The secondary chamber 142 extends from the portion of the casing containing the swab. The secondary chamber 142 is provided with an openable and closable first end 146 having a cap 148 thereon. A second end 150 of the secondary chamber 142 is in atmospheric or gaseous communication with the portion of casing 140 containing the swab 152. FIG. 27 shows a top and side perspective view of the embodiment of FIG. 26 and shows shoulder 154 extending inwardly from casing 144. Shoulder 154 operates to restrict the passageway between secondary chamber 142 and the portion of casing 140 containing the swab 152. This restriction allows the placement of materials into secondary chamber 142 so the materials are in atmospheric communication with swab 152, but physical contact with swab 152 is prevented. An alternative structure to shoulder 154 may be a perforated disk or wire mesh or other such porous structure that would allow gaseous or atmospheric communication between secondary chamber 142 and the portion of casing 140 containing the swab 152 while preventing contact with the swab by the material placed in secondary chamber 142.

FIG. 28 is a top and side perspective view of the embodiment of FIG. 27 and showing cap 148 removed to permit independent access to secondary chamber 142 through first end 146. The independent access permits the introduction or replacement of materials in secondary chamber 142 without disturbing swab 152 and any specimen that may be collected on swab 152. By use of openable and closable first end 146 a material such as a desiccant can be introduced to tube 144 without disturbing swab 152. During use of the sample collection apparatus the desiccant can be replaced through first end 146 as needed without causing disturbance to swab 152. Also, by use of first end 146 to gain access to secondary chamber 142, modifications to the contents of secondary chamber 142 can be made without affecting any tamper evident closure device that has been applied to secure the swab 152 into casing 144.

Figure 29:
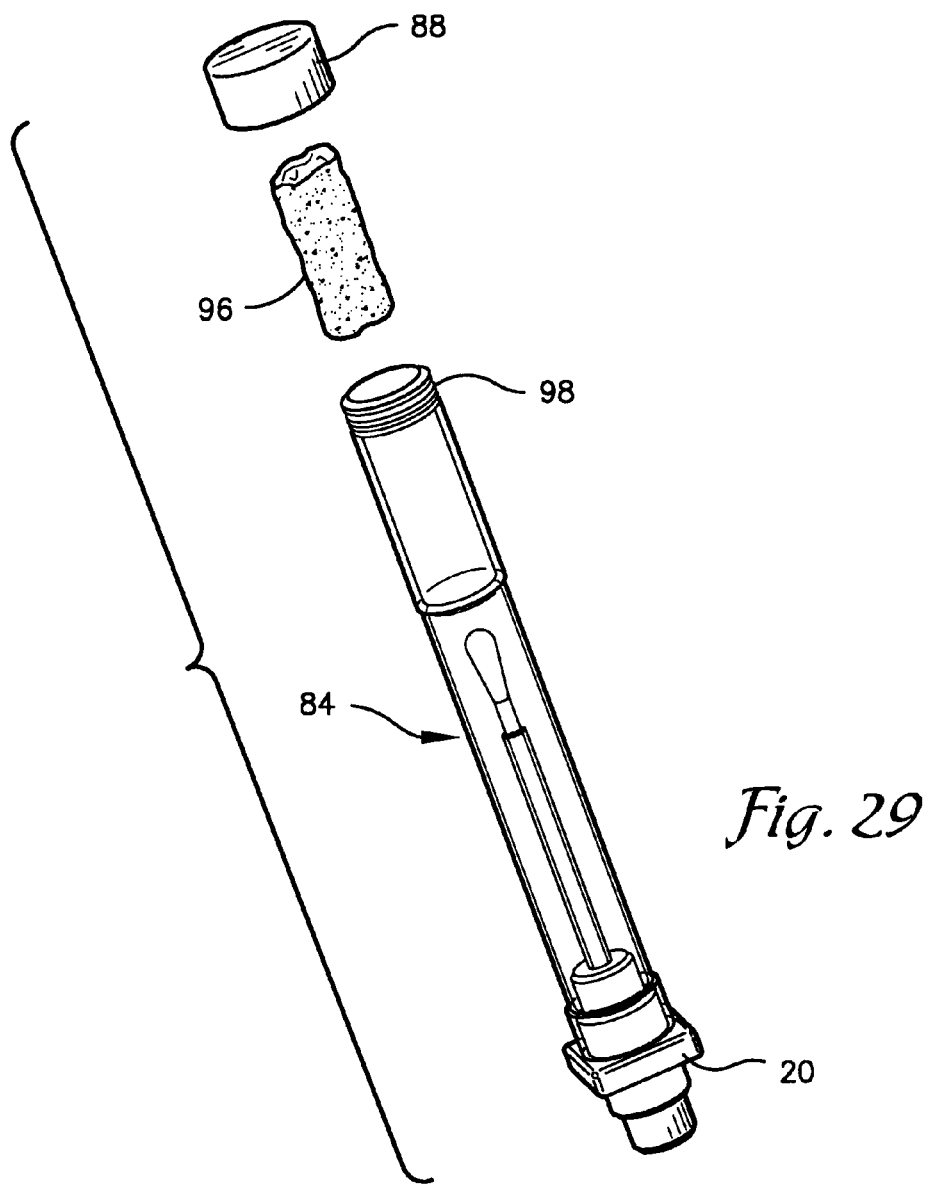
FIG. 29 is a bottom and side partial exploded perspective view of the fifth modified embodiment of the sample collection apparatus of FIG. 26 showing the cap separated from the secondary chamber and a packet of an insert material, such as a desiccant, aligned for insertion into the secondary chamber.

FIG. 29 is a bottom and side partial exploded perspective view of the embodiment of FIGS. 26-28 and showing cap 148 separated from the secondary chamber 142 and a packet 156 of an insert material, such as a desiccant, aligned for insertion into secondary chamber 142. It will be appreciated by those skilled in the art that often it is desirable to have a desiccant or an anti-microbial agent or other such agent proximate to a specimen contained on swab 152. Secondary chamber 142 permits such agents to be introduced into introduced, renewed, and changed out for other agents without disturbance to swab 152 and without damage or disturbance of any chain of custody indicia that may have been applied to cap member 155 (see, FIGS. 16-20). Such chain of custody indicia may be a tape closure or wax seal or other device that would evidence the removal of cap member 155 and such chain of custody indicia are well known in the art. In the present embodiment, cap 148 is removably attached to casing 144 by threads 158, but any will known means of closure may be used to substitute for threads 158.

Detailed Description of the Turbo

As required, detailed embodiments of the present inventions are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

First referring to FIG. 30, the unitized apparatus for collection and/or drying and/or transport and/or analysis device 160 is shown, in one example, with the specimen collector 162 within the housing 164 and the swab 166 situated within the flexible guards 168 (FIG. 31) and between two desiccant packets 170. In this example the device 160 is in a form that can be used for transport or for drying of a specimen that has been applied to swab 166. It can be seen that the swab 166 is positioned between, but not contacted by, desiccant packets 170. Desiccant packets 170 are positioned so to surround swab 166 and to be in close proximity to swab 166. As the proximity of desiccant to moisture has a direct correlation to the rapidity of drying, it will be appreciated that the close, but spaced, proximity of desiccant 170 to swab 166 is particularly efficacious in speeding the drying of moisture that may be on swab 166.

A second example shown in FIG. 30 presents the embodiment in its open position. In the open position, specimen collector 162 has been removed from housing 164 and the cap 172 having swab 166 on shaft 166a having break tube 167 coaxially mounted thereon reversed and inserted into opening 174 of the neck 176 of the housing 164 from which cap 172 and swab 166 on shaft 166a and break tube 167 were just removed. This reversal and reinsertion allows the housing 164 to act as a handle for manipulating the swab 166 of specimen collector portion 162. during the collection of a specimen onto swab 166. The enlarged flat surface of desiccant chamber 180 fits securely into the palm of the hand and also provides a flat surface that will prevent rolling of the device 1660 when it is placed on a surface while the edge of cap 172 maintains the swab 166 separated from any contact with contaminating surfaces.

In FIG. 31 a similar view to that of FIG. 30 is shown with one example presented in a partial exploded view. In the exploded view desiccant chamber cap 178 is separated from the desiccant chamber 180 and the two desiccant packets 170 have been removed from the desiccant chamber 180. Visible within the desiccant chamber 180 are the flexible guards 168 that allow variable spacing of the desiccant packets 170 from the swab 166. It will be appreciated that the flexible nature of flexible guards 168 allows insertion of variously sized desiccant packets 170 into desiccant chamber 180. This is accomplished by the flexible guards 168 being able to bend inwardly toward swab 164 to expand the distance between flexible guards 168 and the walls of desiccant housing 180. Due to this repositionable nature of flexible guards 168, user selectable and variable amounts of desiccant can be introduced by the user into desiccant chamber 180 to speed drying time of a specimen on swab 164 or to permit the replacement of desiccant packets 170 during the use of device 160 and without the need to disturb swab 164 and any specimen thereon.

In FIG. 32 a perspective view is shown of the device 160 of FIGS. 30 and 31 with the desiccant chamber cap 178 placed beside the neck 176 of housing 164 and swab 166 inserted into housing 164. In this position swab 164 is adjacent desiccant 170 for drying and is protected within housing 164 for transport and/or storage. It may be observed that swab 1664 is positioned within and surrounded by flexible guards 168. Desiccant packets 170 shown in FIGS. 30 and 31 have been removed from desiccant chamber 180 for clarity. It will be understood that in FIG. 32, cap 172 has been reinserted into neck 176 to dispose swab 166 on shaft 166a and break tube 167 within housing 164. This positioning places swab 166 disposed between flexible guards 168 within desiccant chamber 180. It may be seen in FIG. 32 that flexible guards 168 extend beyond swab 1664 and prevent objects inserted into desiccant chamber 180 from inadvertent contact with swab 164. Those skilled in the art will appreciate that with desiccant chamber cap 178 removed as shown in FIG. 32 that desiccant chamber 180 is open and accessible. It is in this configuration that desiccant packets 170 can be inserted, removed, renewed or increased or decreased by the used as may be indicated by the needs of the particular specimen on swab 164 or the need to speed up or slow down drying of the specimen on swab 164.

In FIG. 33 the flexible guards 168 and the swab 164 are shown from an end view into desiccant chamber 180. In this view it may be seen that swab 166 is positioned within flexible guards 168 and spaced therefrom so as not to contact flexible guards 168 or the walls of desiccant chamber 180. It will be appreciated that the ends of flexible guard 168 bend inwardly to operate to deflect material entering desiccant chamber 180 from contacting swab 166 and any specimen thereon. Desiccant holding areas 186 extending between flexible guards 168 and the walls of desiccant chamber 180 are shown in FIG. 33. It will be appreciated that as flexible guards 168 may be pushed away from desiccant chamber 180 walls that variously sized desiccant packets 170 can be inserted into desiccant holding areas 186 during drying and/or transport and/or storage. Once the desiccant packets 170 have been operated upon, the desiccant chamber cap 178 may be replaced to again close desiccant chamber 180 to the outside.

Description of Turbo and Gemini and Janus

Referring now to FIG. 34 and embodiment 160, having dual specimen collectors 162 positioned into cap 172 is shown. The dual collectors of the embodiment of FIG. 34 may be used for collection of a specimen using the wet technique and the dry technique of collection while manipulating a single collector 162. The embodiment of FIG. 34 has dual collectors 162 each having a swab of 166 mounted thereon. In use, the operator would moisten one of the two swabs 166 of specimen collector 162 and then apply in turn each swab 166 to the specimen to be collected. It will be appreciated by those skilled in the art that utilizing both dry collection technique and wet collection technique that different components in different quantities of components can be obtained from the specimen. As previously described, the embodiment of FIG. 34 can be placed into housing 164 so it may act as a handle and also so the sample may be dried within housing 164 for storage and transport of the specimen collected upon swabs 166.

Referring now to FIG. 35, and embodiment of a cap 172A is shown having the dual voids therein which permit the positioning and securing of dual swabs within the cap by the insertion of shaft 166A of swab 166 having break tube 167 thereon into cap 172A.

Referring now to FIG. 36, in another embodiment is shown with yet another variation of cap 172, this variation being cap 172B for the embodiment of FIG. 36, the embodiment of cap 172B is provided with three voids for insertion of swab shafts 166A therein, the distribution being a single void on one side of cap 172B and two voids on the opposed side of cap 172B. In the embodiment of FIG. 36, the dual swabs may be placed in either the housing 164 having the ability to retain desiccant packages within housing 164 for the drawing of the swab or the swab 166 may be placed in a more conventional tubular housing 164, which may or may not contain a desiccant. It also will be appreciated that the identification of the end of the device of the embodiment of FIG. 36 having two swabs may be made more readily apparent by utilization of housing 164 for the dual swabs mounted in cap 172B and the end of cap 172B having a single swab may be made more readily apparent to the user by utilizing the tubular housing 164B.

Referring now to FIG. 37, a variation of housings being utilized for the specimen collector 162 of FIG. 36 is shown wherein tubular housings having a desiccant chamber added to the end of the housing 164C is shown.

Referring now to FIG. 38, the desiccant holding housings 164C are shown in place on the embodiment shown in FIG. 37 and in FIG. 36.

The invention claimed is:

1. A specimen collection, drying and transport apparatus comprising:
    a specimen collector comprising:
        a specimen collection swab, said swab connected to a shaft having a first shaft end with said specimen collection swab thereon and a second shaft end connected to a closure, said closure having first and second stopper structures extending from opposed sides of a central member, said first stopper structure connected to the shaft; and
        a break-off tube mounted coaxially on the shaft, the break-off tube having a first end connected to said first stopper structure and a second end terminating at a shaft break-point on said shaft, said shaft-break-point being positioned along said shaft at a location sufficiently spaced from said swab to permit the entire swab to be separated from the shaft when the shaft break-point is pressed against the break-off tube;
    a housing comprising:
        a desiccant chamber;
        a neck extending from the desiccant chamber the neck having an opening providing communication through the neck and into the desiccant chamber for passage of the swab from the neck and into the desiccant chamber;
        a swab isolation area in the desiccant chamber the swab isolation area aligned with the neck to receive the shaft mounted swab from the neck and to position the swab in the swab isolation area of the desiccant chamber;
        a desiccant holding area on at least one side of the swab isolation area the desiccant holding area configured to retain a desiccant packet therein to absorb moisture from a specimen collected on the swab; and
        an openable and closeable bottom on the desiccant chamber configured to permit removal of the desiccant packet from the desiccant holding area and insertion of the desiccant packet into the desiccant holding area while the swab is in the swab isolation area of the desiccant chamber;
    wherein the housing is configured to act both as a handle for the specimen collection portion during specimen collection and to act as a transport container during specimen shipping; and
    wherein the desiccant chamber is configured to dry a specimen collected on the specimen collection portion during storage and shipment of the collected specimen, the desiccant chamber allowing the desiccant to be removed and new desiccant inserted.

2. The apparatus as claimed in claim 1 further comprising retaining structures in the desiccant chamber the retaining structures configured to hold the desiccant packet in the desiccant holding area and away from contact with the swab.

3. The apparatus as claimed in claim 2 wherein the retaining structures are rigid flanges extending from opposed sidewalls of the desiccant chamber.

4. The apparatus as claimed in claim 1 wherein the desiccant packet contains a quantity of desiccant that is sized to correspond to a user selected swab drying time interval.

5. The apparatus as claimed in claim 2 wherein the retaining structures are flexible retainers extending downwardly from a top wall of the desiccant chamber.

6. The apparatus as claimed in claim 2 wherein the retaining structures are flexible projections extending upwardly from the openable and closable bottom.

7. The apparatus as claimed in claim 1 further comprising a unique indicia on the housing for identification of the apparatus.

8. The apparatus as claimed in claim 1 further comprising a reagent vial holder connected to the exterior of the desiccant chamber, the holder having a cylindrical shape and extending upwardly from a shoulder area of the chamber, the chamber shoulder area extending outwardly from the connection of said neck to said desiccant chamber.

9. The apparatus as claimed in claim 8 further comprising a vial for insertion into the reagent vial holder the vial configured to hold a known volume of a reagent for application to the swab.

10. The apparatus as claimed in claim 9 comprising a vial cap holder extending from the outside of the desiccant chamber.

11. The apparatus as claimed in claim 8 wherein the reagent vial holder is a "T" shape projection extending from the desiccant chamber resealable cover and the vial comprises a "T" shaped void registrable with the "T" shape projection.

12. The apparatus as claimed in claim 11 wherein the vial holder is a indention in the desiccant chamber cover.

13. The apparatus as claimed in claim 8 wherein said vial holder is formed integrally with a sidewall of said drying section of said holder.

14. The apparatus as claimed in claim 8 further comprising a projection extending from the neck the projection being configured to receive a vial lid thereon to retain the lid when it is removed from the reagent vial.

15. The apparatus as claimed in claim 8 further comprising a projection extending from the closure the projection being configured to receive a vial lid thereon to retain the lid when it is removed from said reagent vial.

16. The apparatus as claimed in claim 1 having void in the second stopper structure of the closure, the void configured to receive a reagent vial therein.

17. The apparatus as claimed in claim 2 further comprising projections extending from the lid of said reagent vial the projections extending outwardly beyond the sidewall of said closure to permit the projections to be grasped by a user for extraction of the vial from the void.

18. The apparatus as claimed in claim 9 further comprising a selection of vials for insertion into the vial holder said vial selection comprising vials having different reagents compositions and different reagent volumes for substitution into said vial holder to configure the apparatus for different specimen collection applications.

19. The apparatus as claimed in claim 11 wherein the vial holder is a "C-shaped" clamp having friction fit with said vial.

\* \* \* \* \*